US010618937B2

(12) United States Patent
Kim

(10) Patent No.: US 10,618,937 B2
(45) Date of Patent: Apr. 14, 2020

(54) METHOD OF TREATING ALZHEIMER'S DISEASE

(71) Applicant: INDUSTRY-ACADEMIC COOPERATION FOUNDATION GYEONGSANG NATIONAL UNIVERSITY, Gyeongsangnam-do (KR)

(72) Inventor: Myeong Ok Kim, Gyeongsangnam-do (KR)

(73) Assignee: INDUSTRY-ACADEMIC COOPERATION FOUNDATION GYEONGSANG NATIONAL UNIVERSITY, Gyeongsangnam-Do (KR)

(*) Notice: Subject to any disclaimer, the term of this patent is extended or adjusted under 35 U.S.C. 154(b) by 0 days.

(21) Appl. No.: 16/033,725

(22) Filed: Jul. 12, 2018

(65) Prior Publication Data

US 2018/0312540 A1 Nov. 1, 2018

Related U.S. Application Data

(63) Continuation-in-part of application No. PCT/KR2017/000957, filed on Jan. 26, 2017.

(30) Foreign Application Priority Data

Jan. 27, 2016 (KR) .................. 10-2016-0010090

(51) Int. Cl.
| | | |
|---|---|---|
| *A61K 38/00* | (2006.01) | |
| *A61K 38/08* | (2019.01) | |
| *C07K 7/06* | (2006.01) | |
| *A23L 33/18* | (2016.01) | |
| *C07K 14/72* | (2006.01) | |
| *A61P 25/28* | (2006.01) | |
| *A61P 25/18* | (2006.01) | |
| *A61P 25/24* | (2006.01) | |
| *A61P 25/08* | (2006.01) | |
| *A61P 25/16* | (2006.01) | |

(52) U.S. Cl.
CPC ............... *C07K 7/06* (2013.01); *A23L 33/18* (2016.08); *A61K 38/08* (2013.01); *A61P 25/08* (2018.01); *A61P 25/16* (2018.01); *A61P 25/18* (2018.01); *A61P 25/24* (2018.01); *A61P 25/28* (2018.01); *C07K 14/72* (2013.01); *A23V 2002/00* (2013.01)

(58) Field of Classification Search
None
See application file for complete search history.

(56) References Cited

U.S. PATENT DOCUMENTS

2004/0023854 A1  2/2004 Cooper et al.
2014/0271690 A1  9/2014 Wang

FOREIGN PATENT DOCUMENTS

| JP | 5221633 B2 | 6/2013 |
| KR | 10-2012-0046767 A | 5/2012 |
| KR | 10-2014-0042148 A | 4/2014 |
| WO | WO 2011/019815 A2 | 2/2011 |
| WO | WO 2015/083871 A1 | 6/2015 |
| WO | WO 2016/140527 A1 | 9/2016 |

OTHER PUBLICATIONS

International Search Report for PCT/KR2017/000957, dated Apr. 27, 2017.
Lin, Zhuofeng et al., "Fibroblast Ggrowth Factor 21 Prevents Atherosclerosis by Suppression of Hepatic Sterol Regulatory Element—binding Protein-2 and Induction of Adiponectin in Mice", Circulation, [E—pub.] Mar. 20, 2015, vol. 131, No. 21, pp. 1861-1871.
Jean-Francois Emard et al. "Neurodegenerative Diseases and Risk Factors: A Literature Review", Soc. Sci. Med. vol. 40(6), pp. 847-858, 1995.
Sa Shah et al. "Novel osmotin attenuates glutamate-induced synaptic dysfunction and neurodegeneration via the JNK/PI3K/Akt pathway in postnatal rat brain", Cell Death and Disease, vol. 5, e1026; doi:10.1038/cddis.2013.538, 2014.
Sa Shah et al. "Nanoscale-alumina induces oxidative stress and accelerates amyloid beta (Aβ) production in ICR female mice.", Nanoscale, 2015, 7, pp. 15225-15237.
Tahir Ali et al., "Osmotin attenuates amyloid beta-induced memory impairment, tau phosphorylation and neurodegeneration in the mouse hippocampus", Scientific reports, 2015 DOI:10.1038/srep11708.

*Primary Examiner* — Olga N Chernyshev
(74) *Attorney, Agent, or Firm* — The PL Law Group, PLLC

(57) ABSTRACT

A method for preventing, improving or treating a neurological disorder includes administering to a subject a composition including an adiponectin receptor-activating novel peptide as an active ingredient. The adiponectin receptor-activating novel peptide is a peptide consisting of 5 amino acids, and when the adiponectin receptor-activating novel peptide is administered to Alzheimer's model mice, the mice's behavioral changes show that memory and cognitive functions are significantly increased, and APP and amyloid beta (Aβ) proteins are significantly reduced, cytotoxicity does not occur, the proliferation rate of neurons is increased, and cell death is inhibited.

7 Claims, 18 Drawing Sheets

Specification includes a Sequence Listing.

(A)

(B)

(A)

(B)

(C)

SEQUENCE LISTING

```
<160> NUMBER OF SEQ ID NOS: 10

<210> SEQ ID NO 1
<211> LENGTH: 5
<212> TYPE: PRT
<213> ORGANISM: Artificial Sequence
<220> FEATURE:
<223> OTHER INFORMATION: adiponectin receptor-activating peptide

<400> SEQUENCE: 1

Arg Gly Pro Cys Gly
1               5

<210> SEQ ID NO 2
<211> LENGTH: 5
<212> TYPE: PRT
<213> ORGANISM: Artificial Sequence
<220> FEATURE:
<223> OTHER INFORMATION: adiponectin receptor-activating peptide

<400> SEQUENCE: 2

Gly Pro Trp Gly Pro
1               5

<210> SEQ ID NO 3
<211> LENGTH: 5
<212> TYPE: PRT
<213> ORGANISM: Artificial Sequence
<220> FEATURE:
<223> OTHER INFORMATION: adiponectin receptor-activating peptide

<400> SEQUENCE: 3

Gly Pro Cys Tyr Pro
1               5

<210> SEQ ID NO 4
<211> LENGTH: 5
<212> TYPE: PRT
```

```
<213> ORGANISM: Artificial Sequence
<220> FEATURE:
<223> OTHER INFORMATION: adiponectin receptor-activating peptide

<400> SEQUENCE: 4

Gly Pro Cys Trp Pro
1               5

<210> SEQ ID NO 5
<211> LENGTH: 5
<212> TYPE: PRT
<213> ORGANISM: Artificial Sequence
<220> FEATURE:
<223> OTHER INFORMATION: adiponectin receptor-activating peptide

<400> SEQUENCE: 5

Gly Leu Cys Gly Pro
1               5

<210> SEQ ID NO 6
<211> LENGTH: 5
<212> TYPE: PRT
<213> ORGANISM: Artificial Sequence
<220> FEATURE:
<223> OTHER INFORMATION: adiponectin receptor-activating peptide

<400> SEQUENCE: 6

Gly Trp Cys Gly Pro
1               5

<210> SEQ ID NO 7
<211> LENGTH: 5
<212> TYPE: PRT
<213> ORGANISM: Artificial Sequence
<220> FEATURE:
<223> OTHER INFORMATION: 5AA7

<400> SEQUENCE: 7

Gly Pro Arg Gly Pro
1               5

<210> SEQ ID NO 8
<211> LENGTH: 5
<212> TYPE: PRT
<213> ORGANISM: Artificial Sequence
<220> FEATURE:
<223> OTHER INFORMATION: adiponectin receptor-activating peptide

<400> SEQUENCE: 8

Gly Pro Cys Phe Pro
1               5

<210> SEQ ID NO 9
<211> LENGTH: 5
<212> TYPE: PRT
<213> ORGANISM: Artificial Sequence
<220> FEATURE:
<223> OTHER INFORMATION: adiponectin receptor-activating peptide

<400> SEQUENCE: 9

Gly Pro Cys Gly Gln
1               5

<210> SEQ ID NO 10
<211> LENGTH: 5
<212> TYPE: PRT
<213> ORGANISM: Artificial Sequence
```

```
<220> FEATURE:
<223> OTHER INFORMATION: adiponectin receptor-activating peptide

<400> SEQUENCE: 10

Gly Pro Cys Gly Phe
1               5
```

METHOD OF TREATING ALZHEIMER'S DISEASE

CROSS REFERENCE TO RELATED APPLICATIONS

The present application is a continuation in part application to International Application No. PCT/KR2017/000957 with an International Filing Date of Jan. 26, 2017, which claims the benefit of Korean Patent Application No. 10-2016-0010090, filed in the Korean Intellectual Property Office on Jan. 27, 2016, the entire contents of which are incorporated herein by reference.

TECHNICAL FIELD

The present disclosure relates to a composition for the prevention, improvement, or treatment of a neurological disorder, the composition including an adiponectin receptor-activating novel peptide as an active ingredient.

BACKGROUND ART

Degenerative neurological disorder is a disorder in which degenerative changes in the nervous system of the central nervous system cause various symptoms due to the motor and sensory impairment and inhibition of functions such as memory, learning, and computational reasoning. Degenerative neurological disorders occur in a specific part of the nervous system, causing symptoms such as dementia, extrapyramidal abnormality, cerebellar abnormality, sensory disturbance, and movement disorder. In some cases, many parts may be affected at the same time, resulting in complex symptoms. The diagnosis is based on the clinical manifestations of the patient. In this case, it is difficult to diagnose since various other disorders show common clinical symptoms (Soc. Sci. Med. Vol. 40(6), pp. 847-858, 1995).

Dementia, one of the degenerative neurological disorders, is a disorder with general impairment of systemic function, including memory impairment and loss of judgment. Dementia is a geriatric disease: before age 50, its symptoms rarely occur, but after age 60, its frequency of occurrence is gradually increased. As the elderly population increases due to the development of medical technology and quality of life, the number of affected population is rapidly increased not only in Korea but also globally. The number of dementia patients aged 65 years or older registered in 2008 is 421,000, accounting for 8.4% of the total population of the elderly population. In 2030, the number is expected to be 1,135,000, being greater than 9.6% of the total elderly population. In 2008, the Ministry of Health and Welfare researched for the prevalence of dementia and found that there are various onsets of dementia: from among domestic dementias, about 70% are dementia of Alzheimer type, about 25% are dementia of Vascular type, 5% or less are other alcoholic dementia and Parkinson's disease dementia.

Alzheimer disease (AD), the major onset form of dementia, is characterized by two distinct lesions: one is formation of neurofibrillary tangles in the cells caused by hyperphosphorylation and aggregation of tau proteins in neurons of the cortex and hippocampus, and the other one is a plaque formed outside the cells by the aggregation of amyloid β-1/42.

Although the cause of Alzheimer's disease has not yet been clarified, tangles, plaques, or precursors, which are the aggregation form of two proteins involved in aggregation, is deposited on neuronal cells responsible for brain memory and recognition, causing neuronal dysfunction and death, causing Alzheimer.

Genetic and environmental factors play a role in the pathogenesis of senile dementia. Genetic associations include mutations of β-amyloid precursor protein (APP) gene, presenilin-1 (PS1) gene, and presenilin-2 (PS2) gene. These mutations were confirmed in a households suffering from dementia. APP, PS1, PS2, etc. are known to increase the production of β-amyloid (Aβ) precipitated in plaques. As described above, APP, PS1, and PS2 are critical in the pathogenesis of senile dementia, and are currently the subject to be considered in developing new drugs.

Korean Patent Publication No. 2014-0042148 discloses a composition for preventing or treating a degenerative neurological disorder including a bioactive peptide as an active ingredient, Japanese Patent Registration No. 5221633 discloses low molecular weight peptides for the treatment of Alzheimer's disease and other β-amyloid protein fibrillogenesis disorder, and U.S. Patent Publication No. 2014-0271690 discloses a peptide vaccine for the prevention of Alzheimer-type dementia and immunotherapy. However, there has not yet been disclosed a composition for the prevention, improvement, or treatment of a neurological disorder containing an adiponectin receptor-activating novel peptide as an active ingredient according to the present disclosure.

SUMMARY

The present disclosure is introduced in response to the need described above, and it was found that the present disclosure provides a composition for the prevention, improvement, or treatment of a neurological disorder including an adiponectin receptor-activating novel peptide as an active ingredient, wherein the active ingredient is not cytotoxic, reduces the expression levels of APP and Aβ proteins, and enhances the cognitive or memory function of animal models.

The present disclosure provides a health functional food composition for the prevention or improvement of a neurological disorder including at least one peptide selected from peptides consisting of the amino acid sequences of SEQ ID NOS: 1 to 10 as an active ingredient.

The present disclosure also provides a pharmaceutical composition for the prevention or treatment of a neurological disorder including at least one peptide selected from peptides consisting of the amino acid sequences of SEQ ID NOS: 1 to 10 as an active ingredient.

The present disclosure also provides a method of preventing or treating a neurological disorder, the method including administering, to a subject, a composition including at least one peptide selected from peptides consisting of the amino acid sequences of SEQ ID NOS: 1 to 10 as an active ingredient.

The present disclosure relates to a composition for the prevention, improvement, or treatment of a neurological disorder including an adiponectin receptor-activating novel peptide as an active ingredient. The composition according to the present disclosure was administrated to Alzheimer's model mice and then their behavioral changes were identified. The results show that the memory and cognitive functions were remarkably increased, the β-amyloid precursor protein (APP) and amyloid beta (Aβ) proteins were remarkably reduced, and cytotoxicity does not occur, and accordingly, it was identified that the composition is useful for use as a composition for the prevention, improvement, or treatment of neurological disorders. Also, since the adiponectin receptor-activating novel peptide is a peptide consisting of five amino acids, high productivity may be obtained through protein synthesis, leading to an increased industrial availability.

DETAILED DESCRIPTION

Figure 1:
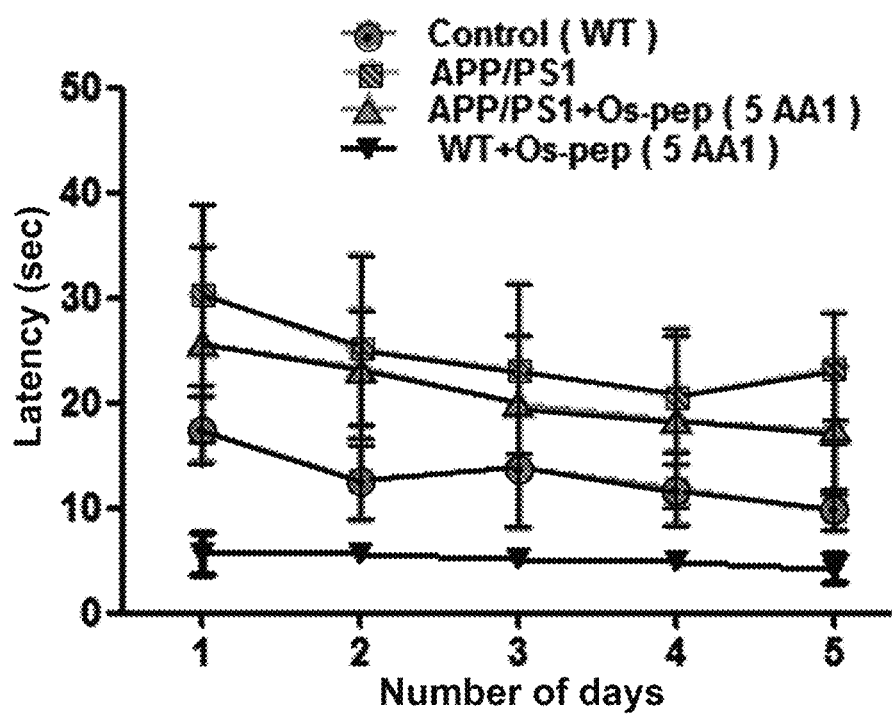
FIG. 1 shows the graph of the latency of the Morris water maze experiment to identify behavioral changes of an Alzheimer's mouse, 45 days after adiponectin receptor-activating novel peptide (5AA1) according to the present disclosure was injected thereto by intraperitoneal injection (IP) administration.

The present disclosure provides a health functional food composition for the prevention or improvement of a neurological disorder including at least one peptide selected from peptides consisting of the amino acid sequences of SEQ ID NOS: 1 to 10 as an active ingredient. The peptides consisting of the amino acid sequences of SEQ ID NOS: 1 to 10 is an adiponectin receptor-activating peptide and a sequence designed through bioinformatics analysis. The peptides consisting of the amino acid sequences of SEQ ID NOS: 1 to 10 may be synthesized by peptide synthesis, but preparation methods for the peptides are not limited thereto.

The neurological disorder may include at least one selected from Alzheimer's disease, dementia, Parkinson's disease, epilepsy, schizophrenia, depression, bipolar disorder, neurogenic disorders, autism, stroke, Lou Gehrig, Huntington's disease, and multiple sclerosis. In one embodiment, the neurological disorder may be Alzheimer's disease, but is not limited thereto. The at least one peptide selected from peptides consisting of the amino acid sequences of SEQ ID NOS: 1 to 10 may be included in an amount of 0.1% by weight to 100% by weight based on the total weight of the composition.

The composition reduces the expression levels of Aβ oligomers or β-amyloid precursor (APP) protein in the hippocampus and cortex of the brain, and increases the expression level of adiponectin receptor 1 (AdipoR1) or p-AMPK protein.

The health functional food composition may be included in any one formulation selected from a beverage, a pill, a tablet, a capsule, and a powder, or may be included in other foods or components of the other foods. The health functional food composition may be appropriately prepared by using a method of the related art.

Examples of a food to which the composition according to the present disclosure is able to be added are meat, sausage, bread, chocolate, candy, snacks, confectionery, pizza, instant noodles, other kinds of noodles, gum, dairy products including ice cream, soups, beverages, tea, drinks, alcoholic beverages, and vitamin complex, and the food may include any food that is conventionally regarded as a health functional food.

The health functional food composition may include various nutrients, vitamins, minerals (electrolytes), synthetic and natural flavoring agents, colorants and enhancers (cheese, chocolate etc.), pectic acid and salts thereof, alkynic acid and salts thereof, organic acids, protective colloid thickeners, pH adjusting agents, stabilizers, preservatives, glycerin, alcohols, carbonating agents used in carbonated drinks, and the like. The health functional food composition may include fruits for the production of natural fruit juices and vegetable drinks. These ingredients may be used independently or in combination, and the health functional food composition may further include various flavoring agents or natural carbohydrates as additional ingredients. The natural carbohydrates are monosaccharides such as glucose and fructose; disaccharides such as maltose or sucrose; polysaccharides such as dextrin or cyclodextrin; and sugar alcohols, such as xylitol, sorbitol, and erythritol. As a sweetening agent, natural sweetening agents, such as Tau Martin and Stevia extract, and synthetic sweetening agents such as saccharin and aspartame may be used.

The present disclosure also provides a pharmaceutical composition for the prevention or treatment of a neurological disorder including at least one peptide selected from peptides consisting of the amino acid sequences of SEQ ID NOS: 1 to 10 as an active ingredient.

The pharmaceutical composition according to one embodiment of the present disclosure may include, in addition to the active ingredient, at least one carrier selected from pharmaceutically acceptable saline, sterilized water, a Ringer's solution, buffered saline, a dextrose solution, a maltodextrin solution, glycerol, ethanol, lactose, dextrose, sucrose, sorbitol, mannitol, starch, acacia rubber, calcium phosphate, alginate, gelatin, calcium silicate, microcrystalline cellulose, polyvinylpyrrolidone, cellulose, syrup, methyl cellulose, methylhydroxybenzoate, propylhydroxybenzoate, talc, magnesium stearate, and mineral oil. The pharmaceutical composition according to one embodiment of the present disclosure may include, in addition to the active ingredient, at least one adjuvant selected from pharmaceutically acceptable antioxidants, buffers, bacteriostats, diluents, surfactants, binders, lubricants, wetting agents, sweetening agents, flavoring agents, emulsifiers, suspending agents, and preservatives.

The pharmaceutical composition may be administered orally or parenterally in accordance with a conventional method. When the pharmaceutical composition is formulated, diluents or excipients, such as a filler, an extender, a binder, a wetting agent, a disintegrant, a surfactant, or the like, may be used. Solid formulations for oral administration include tablets, pills, powders, granules, capsules and the like, and these solid formulations may be prepared by using at least one excipient such as starch, calcium carbonate, sucrose, lactose, gelatin and the like. In addition to these excipients, lubricants such as magnesium stearate and talc may be used. Liquid formulations for oral administration include suspensions, solutions, emulsions, and syrups. These liquid formulations may include, in addition to commonly used simple diluents, such as water and liquid paraffin, various excipients such as wetting agents, sweetening agents, fragrances, preservatives, etc. Formulations for parenteral administration include sterile aqueous solutions, non-aqueous solvents, suspensions, emulsions, freeze-dried preparations, and suppositories. As the non-aqueous solvents and suspensions, propylene glycol, polyethylene glycol, vegetable oil such as olive oil, injectable ester such as ethyl oleate, and the like may be used. Examples of a support for the suppositories are witepsol, macrogol, tween 61, cacao bean, laurin, glycerogelatin, and the like.

The present disclosure also provides a method of preventing or treating a neurological disorder, the method including administering, to a subject, a composition including at least one peptide selected from peptides consisting of the amino acid sequences of SEQ ID NOS: 1 to 10 as an active ingredient. The subject may be an animal or an animal other than a human. In one embodiment, the subject may be a human.

Hereinafter, the present disclosure will be described in detail using the embodiments. These examples are provided herein for illustrative purpose only, and do not limit the scope of the present disclosure, which is obvious to one of ordinary skill in the art.

[Materials and Methods]

1. Novel Peptides

Ten peptides according to the present disclosure were synthesized by Peptron (Korea): 5AA1 (RGPCG; SEQ ID NO: 1), 5AA2 (GPWGP; SEQ ID NO: 2), 5AA3 (GPCYP; SEQ ID NO: 3), 5AA4 (GPCWP; SEQ ID NO: 4), 5AA5 (GLCGP; SEQ ID NO: 5), 5AA6 (GWCGP; SEQ ID NO: 6), 5AA7 (GPRGP; SEQ ID NO: 7), 5AA8 (GPCFP; SEQ ID NO: 8), 5AA9 (GPCGQ; SEQ ID NO: 9), and 5AA10 (GPCGF; SEQ ID NO: 10). These proteins were confirmed to have the purity of 99% by using reverse phase high performance liquid chromatography (HPLC).

2. Classification of Animal Models and Drug Treatment

Male C57BL/6J wild type mice and double transgenic B6.Cg-Tg (APPswe, PSENdE9) 85Dbo Mmjax (APP/PS1) AD-model mice were obtained from Jackson Laboratories (Bar Harbor, Me., USA). The brains of the double transfected mice express Swedish mutation-containing chimeric mouse-human amyloid precursor protein (Mo/HuAPP695swe) and mutant human presenilin 1 protein (PS1-dE9). The mice were fed with an unlimited supply of food and water at an animal breeding ground of a university at a temperature of 23° C., at the relative humidity of 60±10% and in the black and light cycle of 12 h/12 h. When the mice reached 10 months of age, they were transferred to the injection and behavior observation room for 1 week for purification. The maintenance and treatment for mice were performed according to the guidelines of the Animal Ethics Committee (IACUC) issued by Department of Biology, Division of Applied Life Science of Gyeongsang National University in Korea. Experiments according to the present disclosure were conducted according to the guidelines approved by the guidelines of the Animal Ethics Committee (IACUC) issued by Department of Biology, Division of Applied Life Science of Gyeongsang National University in Korea (approval ID: 125).

In the experiments according to the present disclosure, the animals were grouped as follows:

1) Normal group: Wild type (WT) group, which was not treated with the novel peptide according to the present disclosure 2) APP/PS1 transfected group that was not treated with the novel peptide according to the present disclosure 3) APP/PS1 transfected group that was treated with a novel peptide (5AA1 to 5AA4), which is an active ingredient according to the present disclosure 4) Wild-type group that was treated with a novel peptide (5AA1 to 5AA4), which is an active ingredient according to the present disclosure The novel peptide according to the present disclosure was dissolved in bi-deionized distilled water, and administered while being finally included in physiological saline. The novel peptide according to the present disclosure was intraperitoneal injection (IP) administered to APP/PS1 and wild-type (WT) mice in a dose of 5 mg/kg/day at an interval of 2.5 days for 30 days to 45 days. Wild-type mice and APP/PS1 transfected mice were treated with the same volume of physiological saline, and after behavioral analysis, the animal models were sacrificed for further biochemical and immunohistochemical analysis.

3. In Vitro Transfection of SH-SY5Y Cells

1) Plasmids and Cell Lines

The human APPswe/ind gene under the transcriptional control of the SV40 promoter/enhancer linked to the pCAX mammalian expression vector was obtained from addgene; The gene was deposited in the APP reservoir by Dennis Solkoe (plasmid 30145). The plasmid was amplified by DH5alpha strain in LB medium containing 50 µg/ml of ampicillin. The plasmid was purified by using a Qiagen plasmid mini kit (Cat #12143) and digested with EcoRV restriction enzyme and confirmed. The human neuroblastoma cell line SHYSY5Y used in the present in vitro experiments was cultured in DMEM medium containing 10% fetal bovine serum and 1% penicillin-streptomycin antibiotic (stock solutions concentrations of 10,000 U and 10,000 µg/ml, respectively)).

2) APPswe/ind Transfection

SH-SY5Y cells and HT-22 cells were inoculated into a culture flask containing the medium, and cultured until reaching the confluency of 70% to 75%. The pCAX vector with the APPswe/ind gene was transfected for 48 hours by using Lipofectamine 3000 (Life technologies) according to the manufacturers instructions.

APPswe/ind transfected SH-SY5Y cells were treated with novel peptide for 4 hours, followed by 3-[4, 5-dimethylthiazol-2-yl]-2,5-diphenyl tetrazolium bromide (MTT) analysis and Western blot analysis.

Example 1. Behavioral Analysis

Behavioral studies were performed by using the Morris water maze (MWM) test and the Y-maze test, each with 13 mice per group.

1) Morris Water Maze Test

The Morris Underwater Maze Test System was constructed as a circular water tank with a diameter of 100 cm and a height of 40 cm containing 15.5 cm depth of water (temperature of 23±1° C.) which was opaque with white ink added. A transparent escape platform (10 cm in diameter, 20 cm in height) was hidden 1 cm below the water surface, and placed in the center of one of the quadrants. Each mouse was trained daily for five consecutive days by using three quadrants of rotational starting and one platform hidden in one quadrant. The delay time for escaping from the water maze (the time to find the hidden escape platform) was calculated for each trial. Twenty-four hours on the fifth day, a probe experiment was conducted to evaluate memory enhancement. For the probe experiment, the platform was removed, each mouse was allowed to freely swim for 60 seconds, the amount of time the mouse spent in the target quadrant was measured, and the number of platform positions the mouse passed by (where the platform was located during the hidden platform training). The time spent in the target quadrant was used as a reference for determining the degree of memory enhancement. All data were recorded by using video-tracking software (SMART, Panlab Harward Apparatus, Bioscience Company, Holliston, Mass., USA).

The results show, as illustrated in FIG. 1, that in the case of normal mice, latency, which is the time for the escape from the water maze (time to find the hidden escape platform), was less than 10 seconds, and in the case of APP/PS1 model mice, the latency was increased to about 30 seconds. Although the latency was slightly decreased by training for 5 days, the decrease was within the error range. However, in the case of APP/PS1 model mice treated with the adiponectin receptor-activating novel peptide (5AA1) according to the present disclosure, the latency time was decreased to 25 to 20 seconds, and in the case of the normal mouse treated with the adiponectin receptor-activating novel peptide (5AA1) according to the present disclosure, the latency time was less than 10 seconds.

Figure 2:
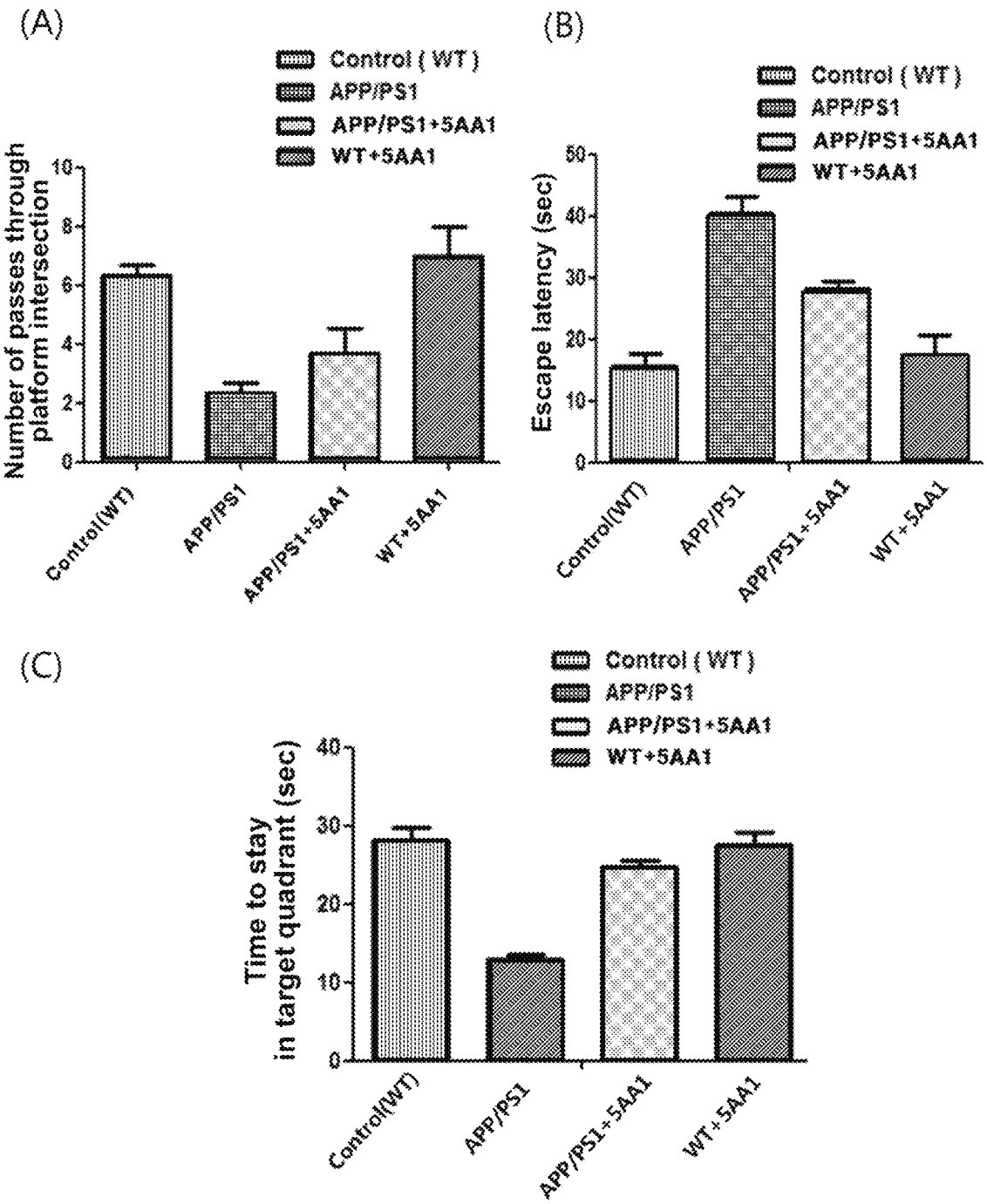
FIG. 2 shows results of a probe test of the Morris water maze experiment to identify behavioral changes of an Alzheimer's mouse, 45 days after adiponectin receptor-activating novel peptide (5AA1) according to the present disclosure was injected thereto by IP administration: (A) the number of passes through platform intersection, (B) escape latency, and (C) time to stay in the target quadrant.

Also, as shown in FIG. 2, compared to the normal mouse, the APP/PS1 model mice showed a significant decrease in the time for staying in the place where the platform was located, and when the APP/PS1 model mice were treated with 5AA1, the time for staying where the platform was located was increased compared to the APP/PS1 model mice.

2) Y-Maze Test

The Y-maze was made of black painted wood, and each arm of the Y-maze had a length of 50 cm, a height of 20 cm, and a width between a floor and the top of 10 cm. Each mouse was placed in the center of the maze device, and was allowed to move freely in the maze during three 8-minute sessions. The series of arm entries were visually observed. Spontaneous alteration was defined as the case in which the mice sequentially entered three different arms in the overlapping triplet sets.

Alteration behavior ratio (%) was calculated as [set of overlapping triplets (consecutive entry into 3 different arms)/total entry−2]×100. The higher spontaneous alternation behavior ratio was considered as improved memory function.

Figure 3:
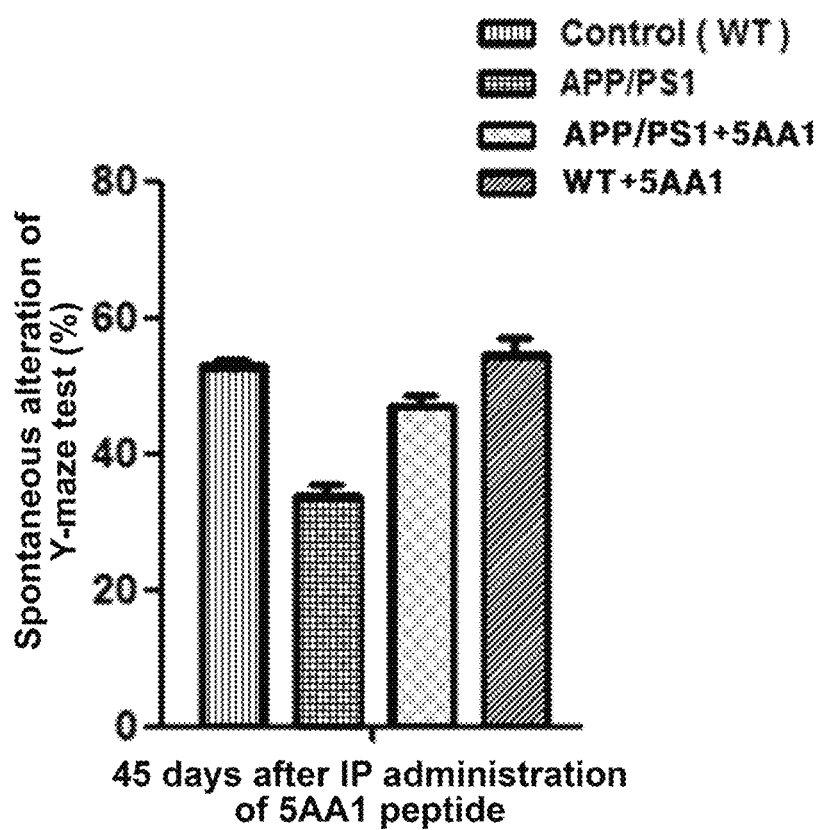
FIG. 3 shows results of a spontaneous alteration of Y-maze test (%) to identify behavioral changes of an Alzheimer's mouse, 45 days after adiponectin receptor-activating novel peptide (5AA1) according to the present disclosure was injected thereto by IP administration.

Results of the Y-maze test, as shown in FIG. 3, show that the spontaneous alteration was reduced in the APP/PS1 model mice as compared with the normal mice, and restored by treatment with 5AA1.

From behavioral analysis of APP model mice, it was confirmed that the treatment with the novel peptide according to the present disclosure improves cognition or memory.

Example 2. Change in Cell Viability According to the Treatment with Peptides (5AA1 to 5AA4)

MTT assay was performed to measure the survival rate of cells treated with various concentrations of adiponectin receptor-activating novel peptide (5AA1). The cells were inoculated at $1 \times 10^5$ cells/well in a 96-well plate containing 200 μl of Dulbecco's modified Eagle's medium (DMEM). After 70% of cell confluence, SH-SY5Y cells were treated with 0.5 μM, 1 μM, 5 μM, 10 μM, and 20 μM of adiponectin receptor-activating novel peptide, and then cultured for 4 hours. At the end of the treatment, MTT (5 mg/ml in PBS) was added to each well, and the plate was cultured at a temperature of 37° C. for 4 hours. The formazan dissolved in dimethyl sulfoxide (DMSO) was added to the well and the plate was stirred in the agitator for 10 to 20 minutes. Then, the absorbance was measured at a wavelength of 550 nm to 570 nm (L1) and 620 nm to 650 nm (L2) by using a scanning microplate reader.

The L2 absorbance was measured for cell residuals and well imperfections, and the corrected absorbance (Abs.=L1−L2) of each well was calculated from 100× the absorbance of treated well/absorbance of the control well, and was used to measure the cell viability.

Figure 4:
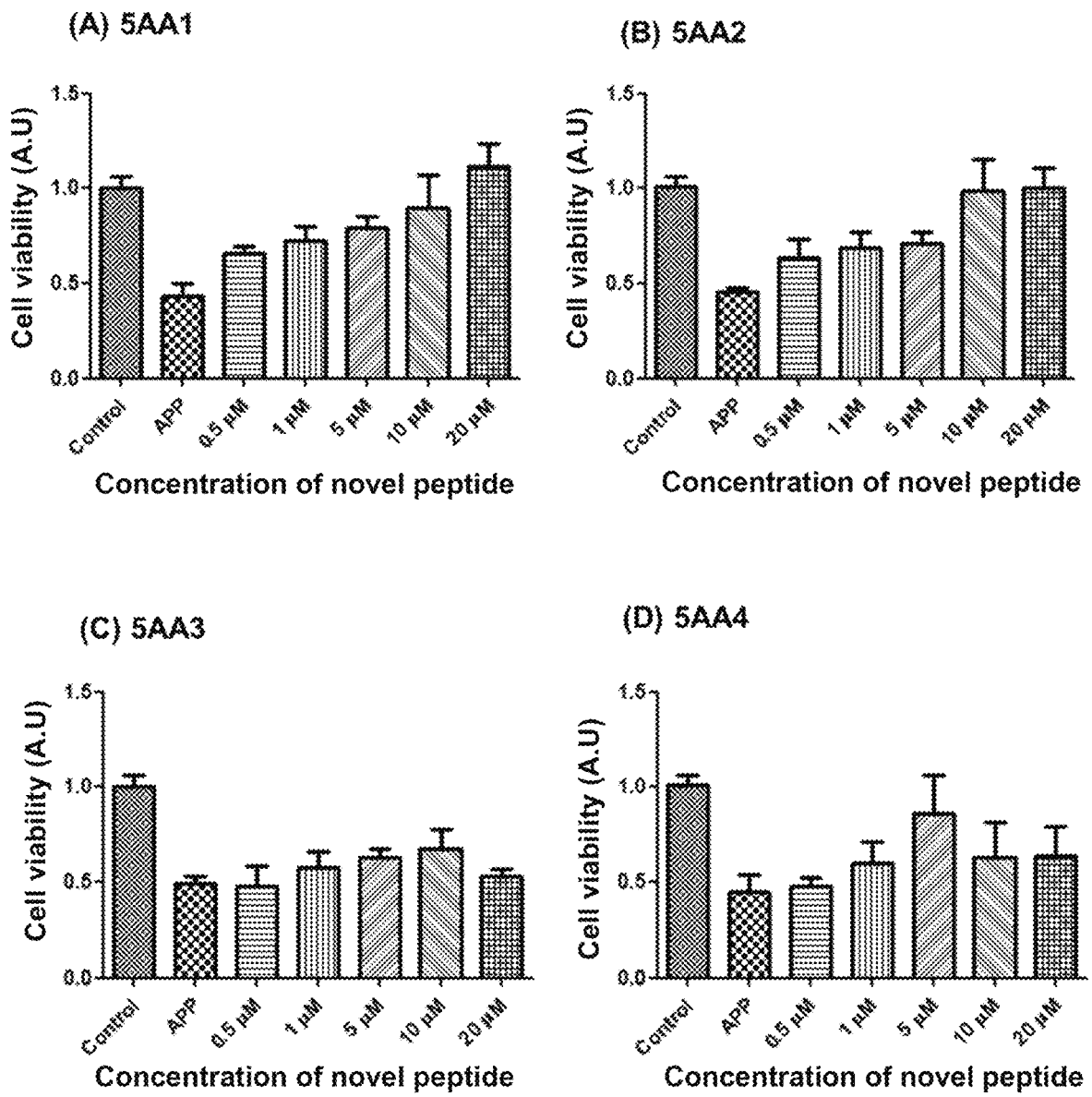
FIG. 4 shows the survival rate of β-amyloid precursor protein (APP)-transfected SHS5Y human neurons after the SHS5Y human neurons were treated with 5AA1, 5AA2, 5AA3, or 5AA4 peptide at the concentration of 0.5, 1, 5, 10, and 20 μM, wherein Control represents normal SHS5Y human neurons, and APP represents APP-transfected SHS5Y human neurons which were not treated with 5AA1, 5AA2, 5AA3, or 5AA4 peptide.

As shown in FIG. 4, when the novel peptides 5AA1 and 5AA2 according to the present disclosure were used, the cell viability decreased in APP-transfected cells was concentration-dependently increased, and when 5AA3 and 5AA4 were used, the cell viability of the treated groups was increased compared to the APP group, although the increase was not dependent on concentration. Accordingly, it was confirmed that the adiponectin receptor-activating novel peptides (5AA1-5AA4) according to the present disclosure has no cytotoxicity.

Example 3. Western Blot Analysis

Protein concentrations were measured by using a BIO-RAD protein assay kit (BIORAD LABORATORIES, CA, USA). Equal amounts of protein (15 to 25 μg) were electrophoresed under the same experimental conditions using 4 to 12% BLOT™ minigel and MES SDS electrophoresis buffer (running buffer) 1×(NOVEX, LIFE TECHNOLOGIES, Kiryat Shmona, Israel), and a broad range prestained protein marker (GANGNAM STAIN™, Intron Biotechnology) was used as the control for the molecular size. To reduce nonspecific binding, the membranes used were blocked with 5% (w/v) skim milk and reacted with a primary antibody (a 1:1000 dilution) overnight at 4° C. After an appropriate reaction with a horseradish peroxidase (HRP)-binding secondary antibody, proteins were detected by using an ECL detection reagent (AMERSHAM PHARMECIA BIOTECH, Uppsala, Sweden) according to the manufacturer's instructions. The X-ray film was scanned and the optical density of the band was analyzed using a densitometry using a computer-based Sigma Gel program, version 1.0 (SPSS, Chicago, Ill., USA).

For use as the primary antibody, anti-amyloid β (Aβ), anti-APP, anti-AdipoR1 (Adiponectin receptor 1), anti-phospho-AMPK, anti-SNAP-25 (Synaptosomal-Associated Protein 25), anti-SAP-102, anti-Syanpatophysin, phospho-Tau (Ser 413), anti-p-mTOR, anti-p-ULK1, and anti-β-actin were used.

Figure 5:
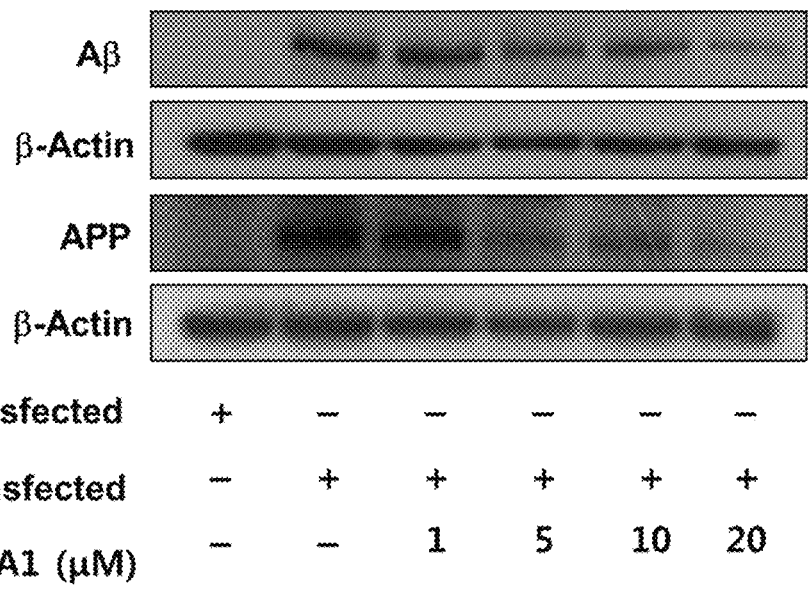
FIG. 5 shows a substantial decrease in APP and Aβ proteins when APP-transfected HT-22 cells were treated with adiponectin receptor-activating novel peptide (5AA1) having the concentration of 1 μM, 5 μM, 10 μM, or 20 μM. *** indicates that the expression of APP and Aβ proteins was statistically significantly increased in APP-transfected HT-22 cells compared to non-transfected HT-22 cells, and ### indicates that the expression of APP and Aβ proteins was statistically significantly reduced in APP-transfected HT-22 cells which were treated with 5AA1 compared to APP-transfected HT-22 cells.
Figure 5:
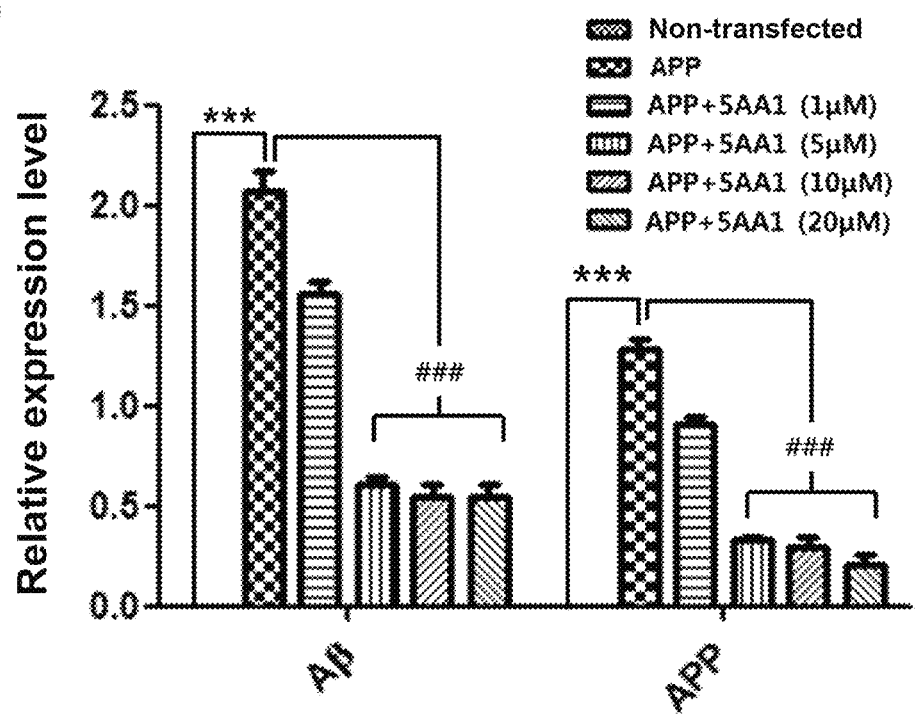
Figure 6:
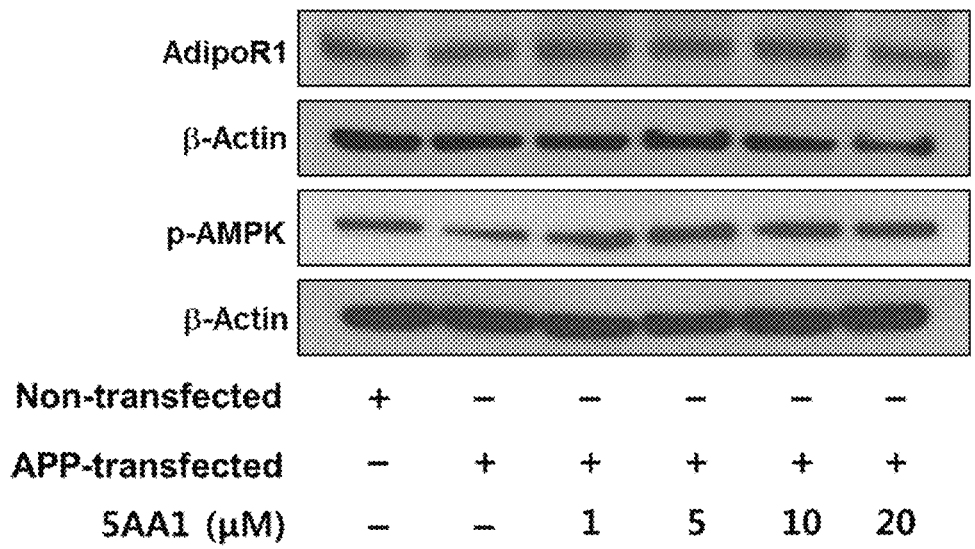
FIG. 6 shows a substantial increase in the expression of adiponectin (adipoR1) and p-AMPK protein in APP-transfected HT-22 cells when treated with adiponectin receptor-activating novel peptide (5AA1) having the concentration of 1 μM, 5 μM, 10 μM, or 20 μM. *** indicates that the expression of adiponectin (adipoR1) and p-AMPK proteins was statistically significantly decreased in APP-transfected HT-22 cells compared to non-transfected HT-22 cells, and ### indicates that the expression of adiponectin (adipoR1) and p-AMPK proteins was statistically significantly increased in APP-transfected HT-22 cells which were treated with 5AA1 compared to APP-transfected HT-22 cells.
Figure 6:
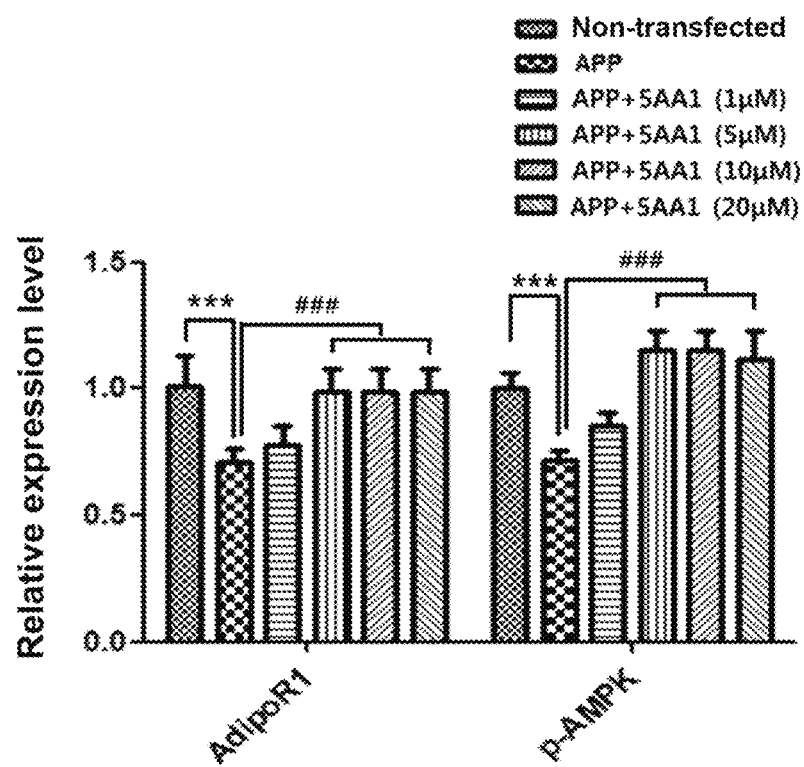

Western blot analysis of proteins isolated from HT-22 cells revealed, as illustrated in FIG. 5, that the expression levels of amyloid β (Aβ) and β-amyloid precursor protein (APP) proteins were significantly reduced. (B) of FIG. 5 shows the quantification value obtained by normalizing the result of (A) of FIG. 5 with β-actin. Referring to (B) of FIG. 5, it was confirmed that in the normal cells, amyloid β (Aβ) and APP proteins were hardly expressed, and in the APP-transfected cells, the expression of APP proteins were significantly increased, and when the APP proteins were treated with the novel peptide (5AA1) according to the present disclosure, the expression level was reduced. In the case of APP-transfected cells, when treated with the adiponectin receptor-activating novel peptide (5AA1) according to the present disclosure, the cells expressed more AdipoR1 and p-AMPK proteins (FIG. 6).

Figure 7:
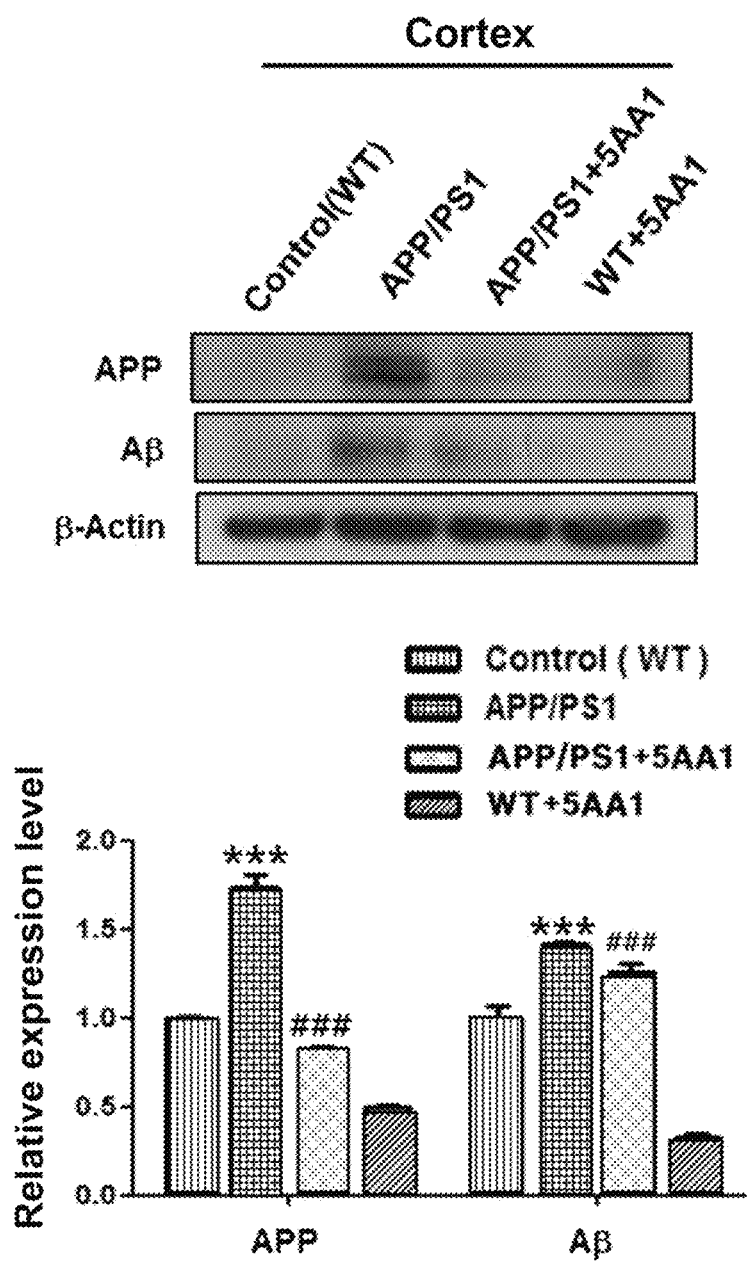
FIG. 7 shows a decrease in APP and amyloid-β oligomer (Aβ oligomer), which had been increased in the cortex of APP/PS1 mice, when the mice were treated with adiponectin receptor-activating novel peptide (5AA1) according to the present disclosure. *** indicates that APP and amyloid-β oligomer (Aβ oligomer) were statistically significantly increased in the cortex of APP/PS1 mice compared to Control, and ### indicates that APP and amyloid-β oligomer (Aβ oligomer) were statistically significantly reduced in the cortex of APP/PS1 mice when treated with 5AA1 compared to Control.
Figure 8:
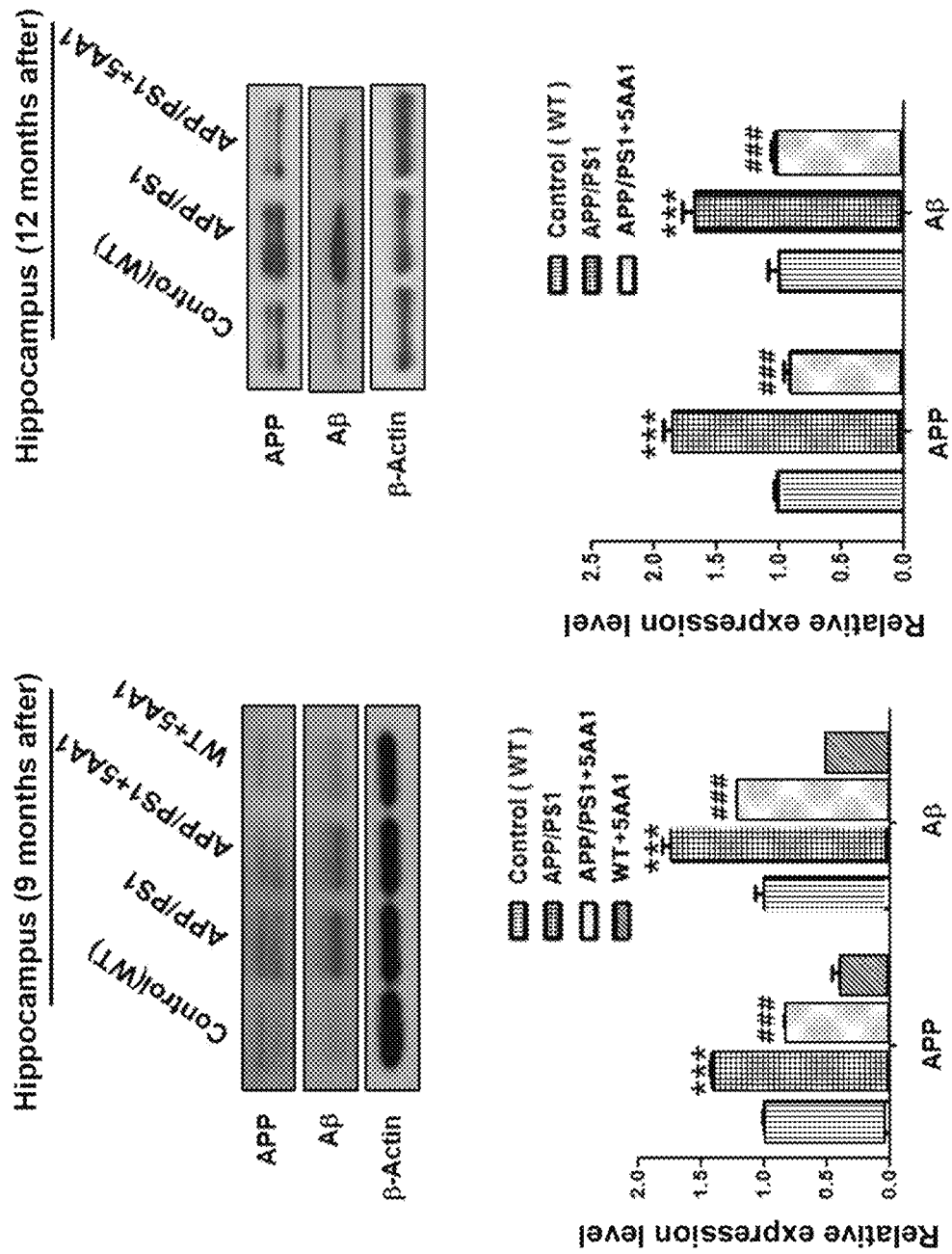
FIG. 8 shows a decrease in the APP and amyloid-β oligomer (Aβ oligomer) increased in the hippocampus of APP/PS1 mice, due to the treatment with adiponectin receptor-activating novel peptide (5AA1) according to the present disclosure, 9 months and 12 months after the induction of APP/PS1 mice. *** indicates that APP and amyloid-β oligomer (Aβ oligomer) were statistically significantly increased in the hippocampus of APP/PS1 mice compared to Control, and ### indicates that APP and amyloid-β oligomer (Aβ oligomer) were statistically significantly reduced in the hippocampus of APP/PS1 mice when treated with 5AA1 compared to Control.

Although the expressed levels of AAP and Aβ isolated from the cortex and hippocampus of the APP/PS1 model mice were substantially increased, the increase in the expression level was suppressed due to the treatment with the adiponectin receptor-activating novel peptide according to the present disclosure (FIG. 7), and even 9 months and 12 months after the treatment with adiponectin receptor-activating novel peptide (5AA1), the expression levels of AAP and Aβ in the hippocampus were decreased (FIGS. 7 and 8).

Figure 9:
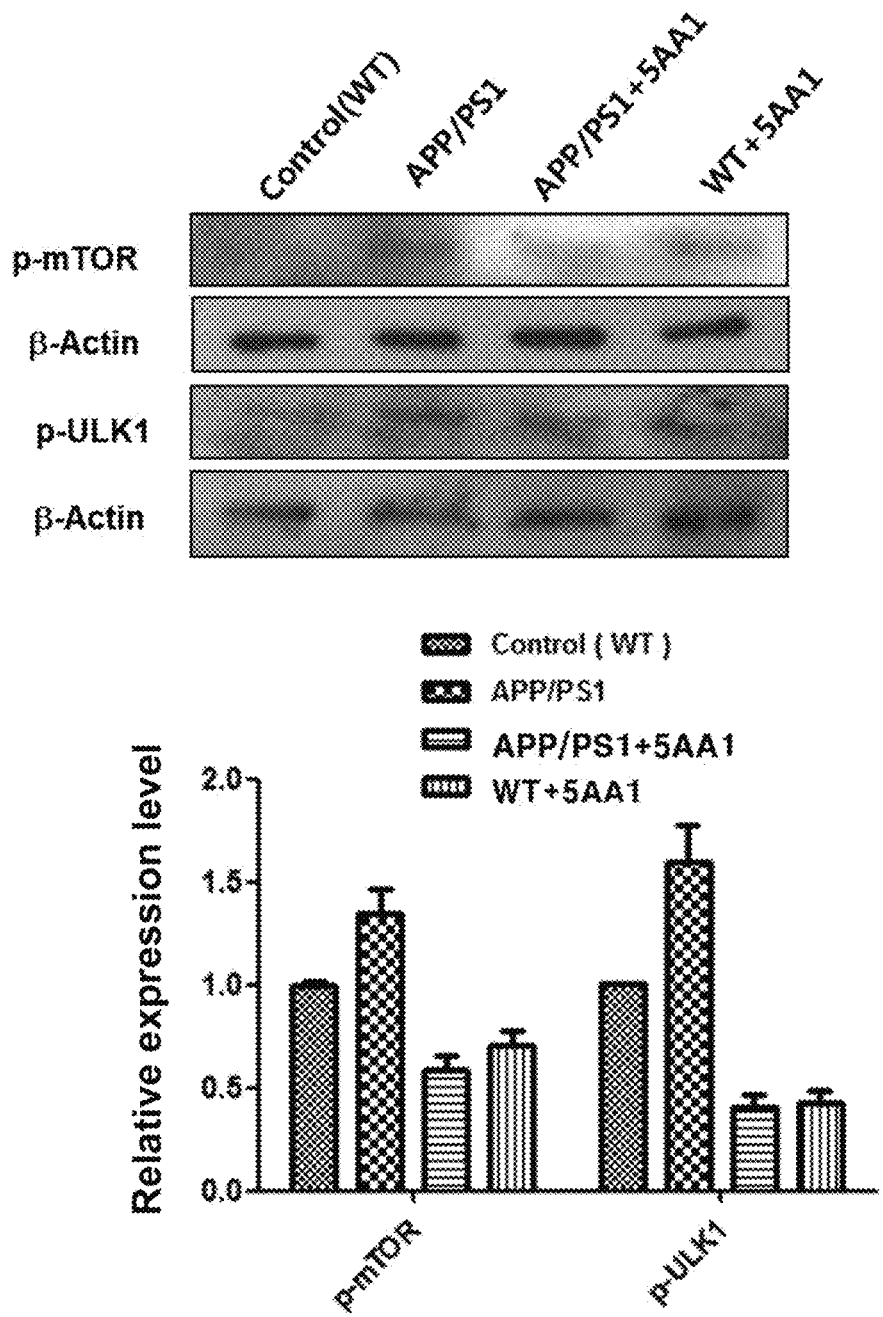
FIG. 9 shows the suppression of the expression of p-mTOR and p-ULK1 proteins increased in APP/PS1 mice, due to the treatment with adiponectin receptor-activating novel peptide (5AA1) according to the present disclosure.

It was confirmed that expression of p-mTOR and p-ULK1 proteins isolated from APP/PS1 model mice was decreased (FIG. 9). These changes in the expression level indicate that the adiponectin receptor-activating novel peptide according to the present disclosure regulates neuronal signal transduction.

Figure 10:
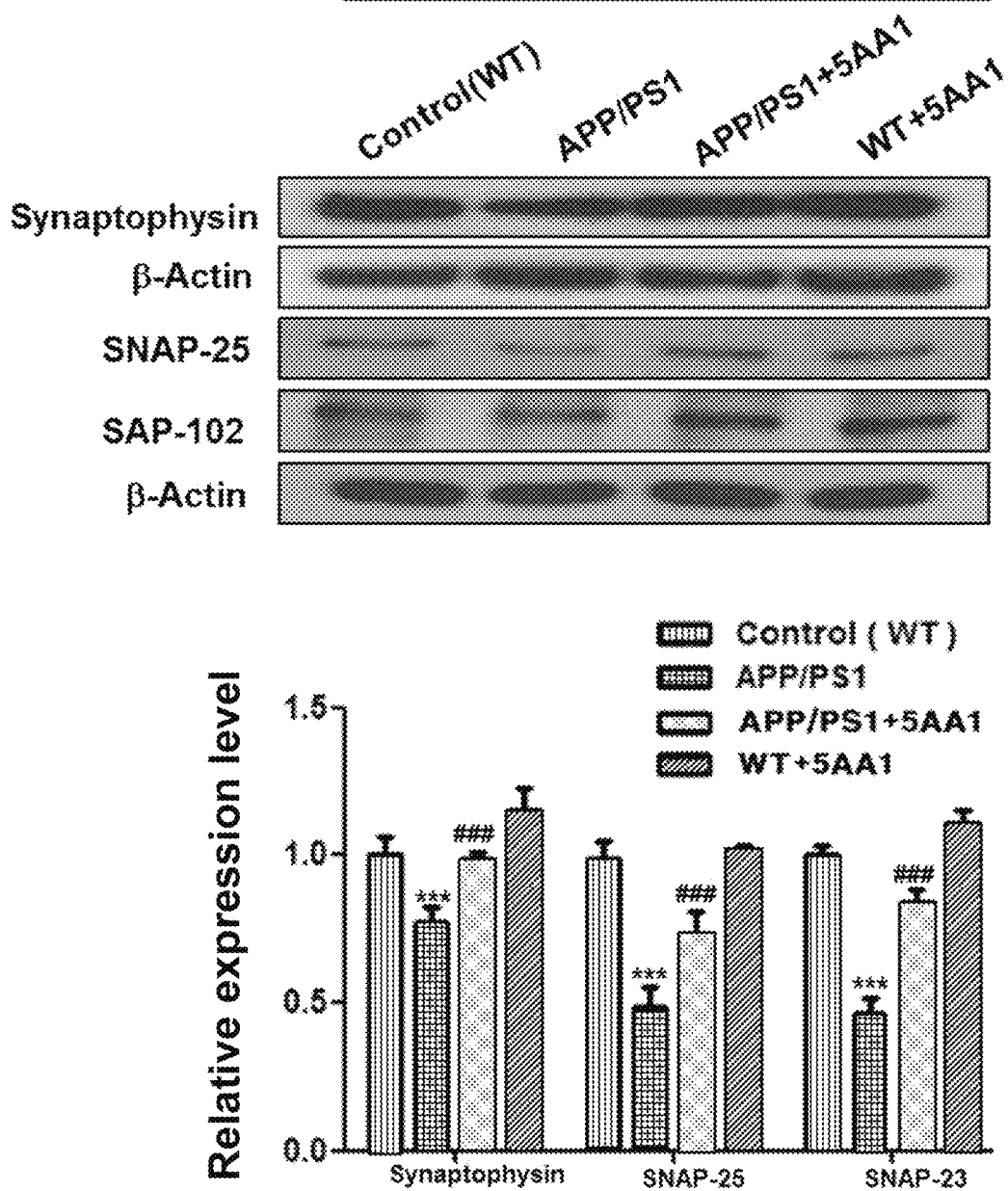
FIG. 10 shows the expression levels of Synaptophysin, SNAP-25, and SAP-102 expressed when the synaptic function of the hippocampus of APP/PS1 mice was enhanced due to the treatment with adiponectin receptor-activating novel peptide (5AA1) according to the present disclosure, 9 months after the induction of APP/PS1 mice.
Figure 11:
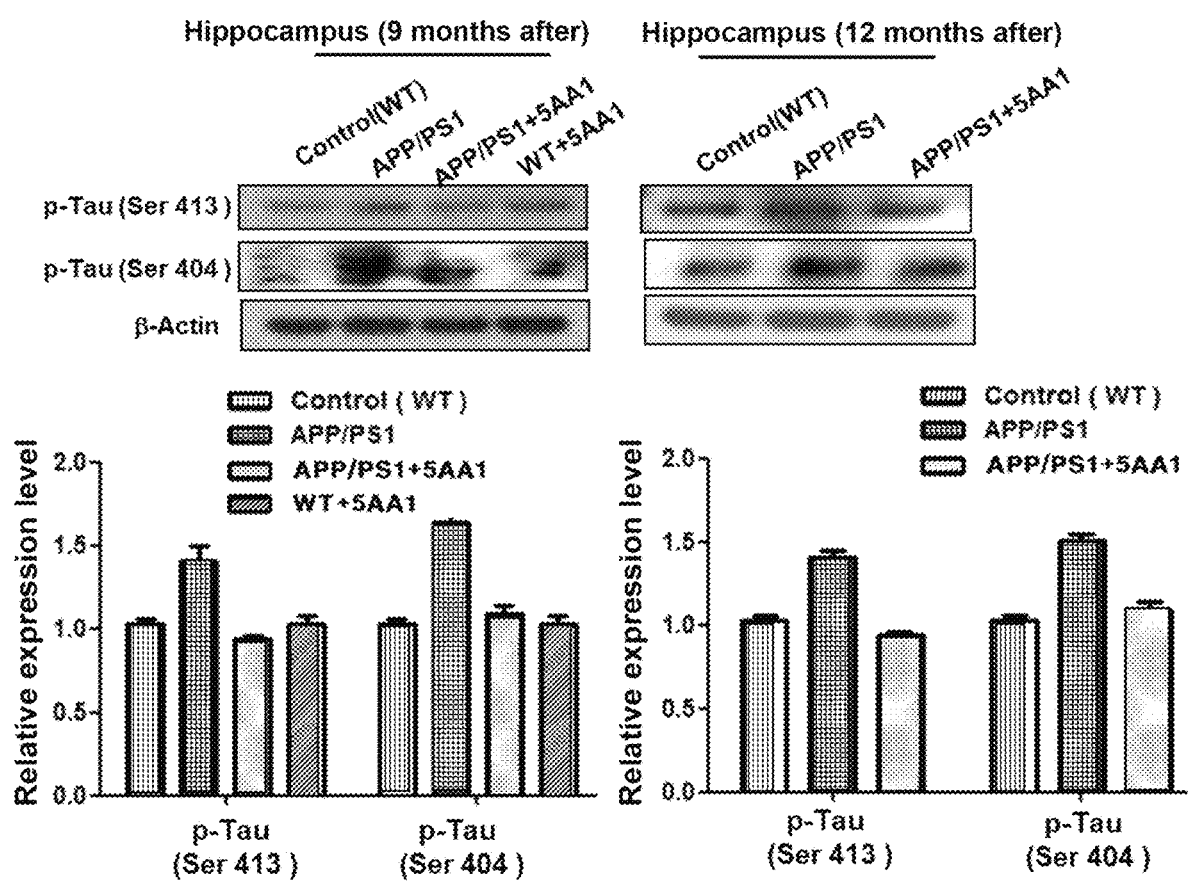
FIG. 11 shows the change in the expression levels of p-Tau (Ser413) and p-Tau (Ser404) in the hippocampus of APP/PS1 mice due to the treatment with adiponectin receptor-activating novel peptide (5AA1) according to the present disclosure, 9 months after the induction of APP/PS1 mice.
Figure 12:
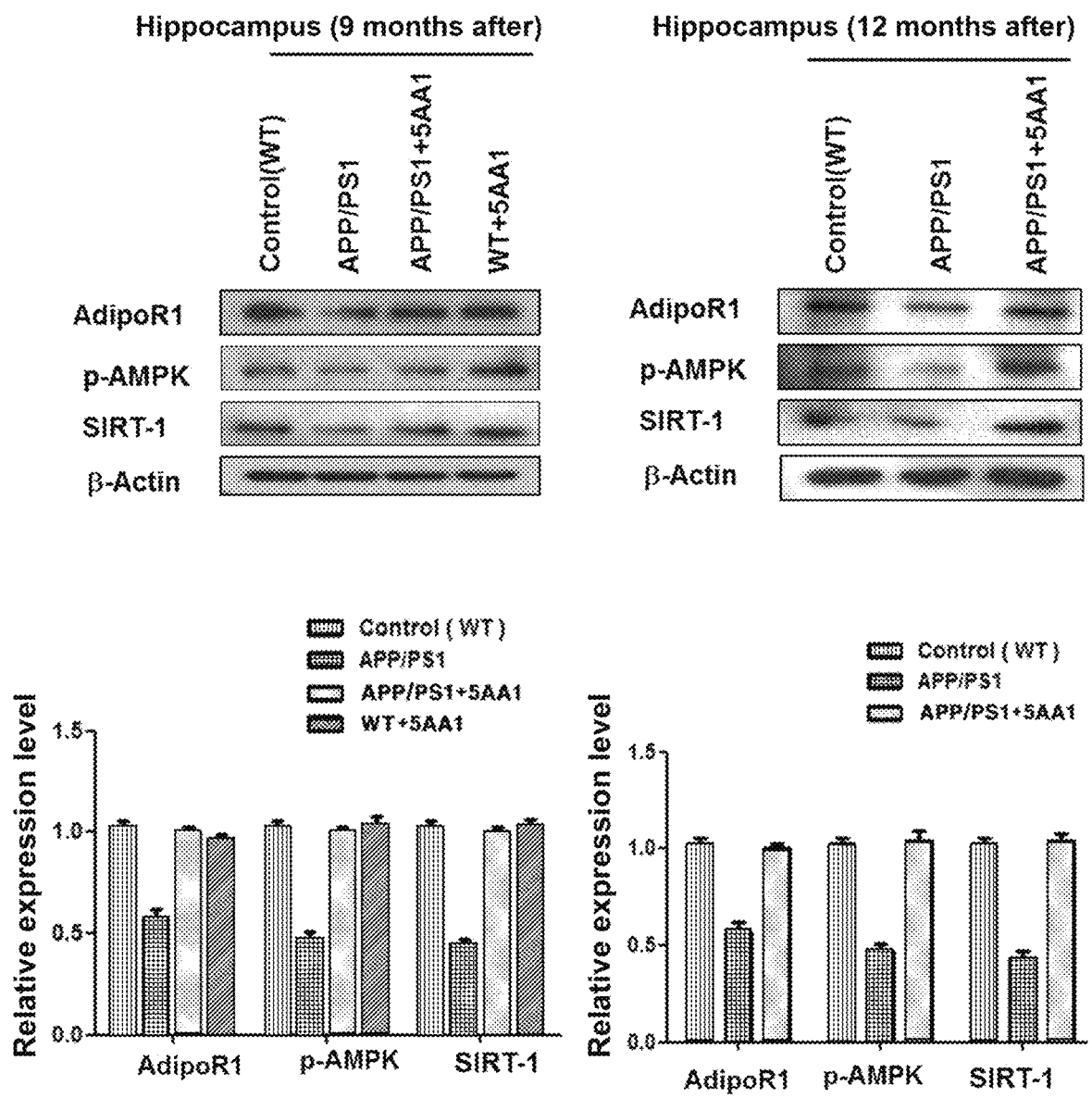
FIG. 12 shows an increase in the expression levels of AdipoR1, p-AMPK, and SIRT-1 reduced in the hippocampus of APP/PS1 mice due to the treatment with adiponectin receptor-activating novel peptide (5AA1) according to the present disclosure, 9 months and 12 months after the induction of APP/PS1 mice.

In addition, the expression levels of SNAP-25, SAP-102 and Synaptophysin proteins, proteins that enhance synaptic function in the hippocampus, were reduced in APP/PS1 transfected cells, Even 9 months and 12 months after the treatment with adiponectin receptor-activating novel peptide (5AA1), the expression levels remained at the remarkably increased levels (FIG. 10) The expression levels of p-Tau (Ser413) and p-Tau (Ser404) proteins remained at the remarkably decreased levels (FIG. 11), and the expression levels of AdipoR1, pAMPK and SIRT-1 remained at the remarkably increased levels (FIG. 12).

Example 4. Immunofluorescence Analysis of Brain after Intraperitoneal Injection and Tail Vein Injection of Adiponectin Receptor-Activating Novel Peptide Using Animal Model Adiponectin receptor-activating novel peptide (5AA1) was IP administered to 10 week old APP/PS1 mice once every 2.5 days for 45 days, and then, to prepare a slide section, the brains of the mice were fixed by transcardial perfusion of ice-cold 4% paraformaldehyde. The brains were fixed in 4% paraformaldehyde for 72 hours, and then, transferred to 20% sucrose and maintained at a temperature of 4° C. for 72 hours. The brains were placed in an optimal cutting temperature (OCT) compound (A.O., USA), frozen in liquid nitrogen, and sectioned into coronal plane (14 µm) in CM 3050C cryostat (Leica, Germany). Pictures of tissue sections were taken on ProbeOn Plus charged slides (Fisher, USA).

Immunofluorescence analysis was performed by using minor modifications of the method described in the existing study (Shah et al., 2014; Shah et al., 2015). Slides containing tissue sections were washed twice with a 0.01 M PBS solution for 15 minutes. Proteinase K was added to the tissue sections, which were then cultured at a temperature of 37° C. for 5 minutes. The tissue sections were then reacted in a blocking solution (5% normal goat serum, 0.3% Triton X-100, PBS) for 1 hour. The slides were reacted overnight with the primary antibody (the same antibody used in the 'Western blot analysis') and then reacted with secondary TRITC- or FITC-conjugated antibodies (diluted 1:50 in PBS; Santa Cruz) at room temperature for 90 minutes. The slides were dipped in Prolong Antifade reagent (Molecular Probe, Eugene, Oreg., USA) and stained. All stained slides were analyzed with a confocal laser scanning microscope (Flouview FV 1000). Amyloid plaques were visualized in brain slices after Thioflavin S staining. The brain slices were washed twice with 0.01 M PBS for 10 minutes, and then immersed in fresh 1% Thioflavin S solution at room temperature for 10 minutes. The brain slices were then immersed in 70% ethanol for 5 minutes, then washed twice with water, counterstained with propidium iodide (PI) and covered with cover glass.

Morphological analysis and signals were analyzed with Image J software (open source software provided by the US NIH), and the analysis results were expressed as IOD (Integral Optical Density). The ratio of the amyloid deposit site in the proposed area was also quantified by using Image-J software.

Figure 13:
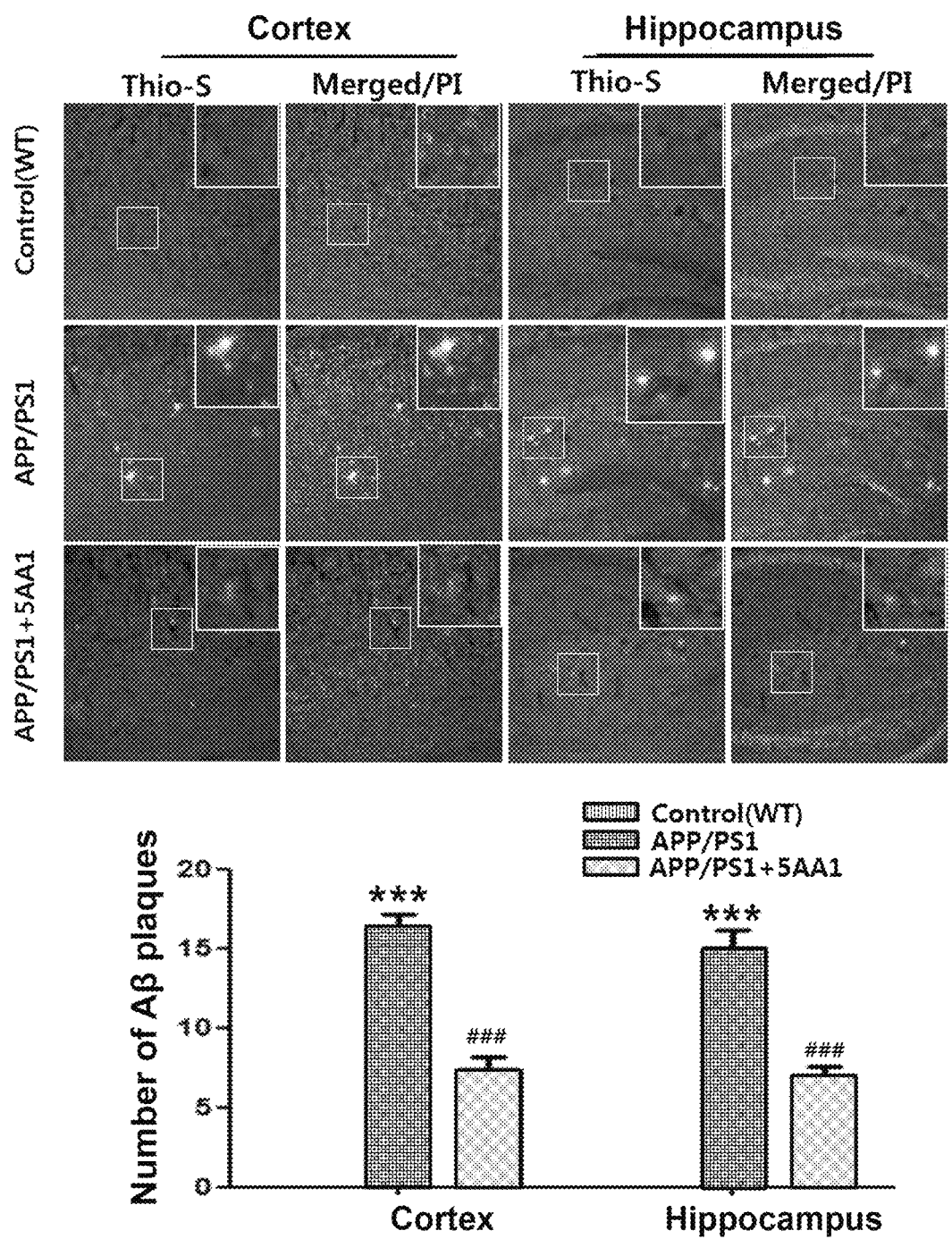
FIG. 13 shows a decrease in amyloid-β oligomer (Aβ oligomer) plaques generated in the cortex and hippocampus of APP/PS1 mice due to the treatment with adiponectin receptor-activating novel peptide (5AA1) according to the present disclosure.

The results show, as illustrated in FIG. 13, that the amyloid β plaque generated in the cortex and hippocampus of the brain was remarkably reduced due to the treatment with adiponectin receptor-activating novel peptide (5AA1) according to the present disclosure.

Figure 14:
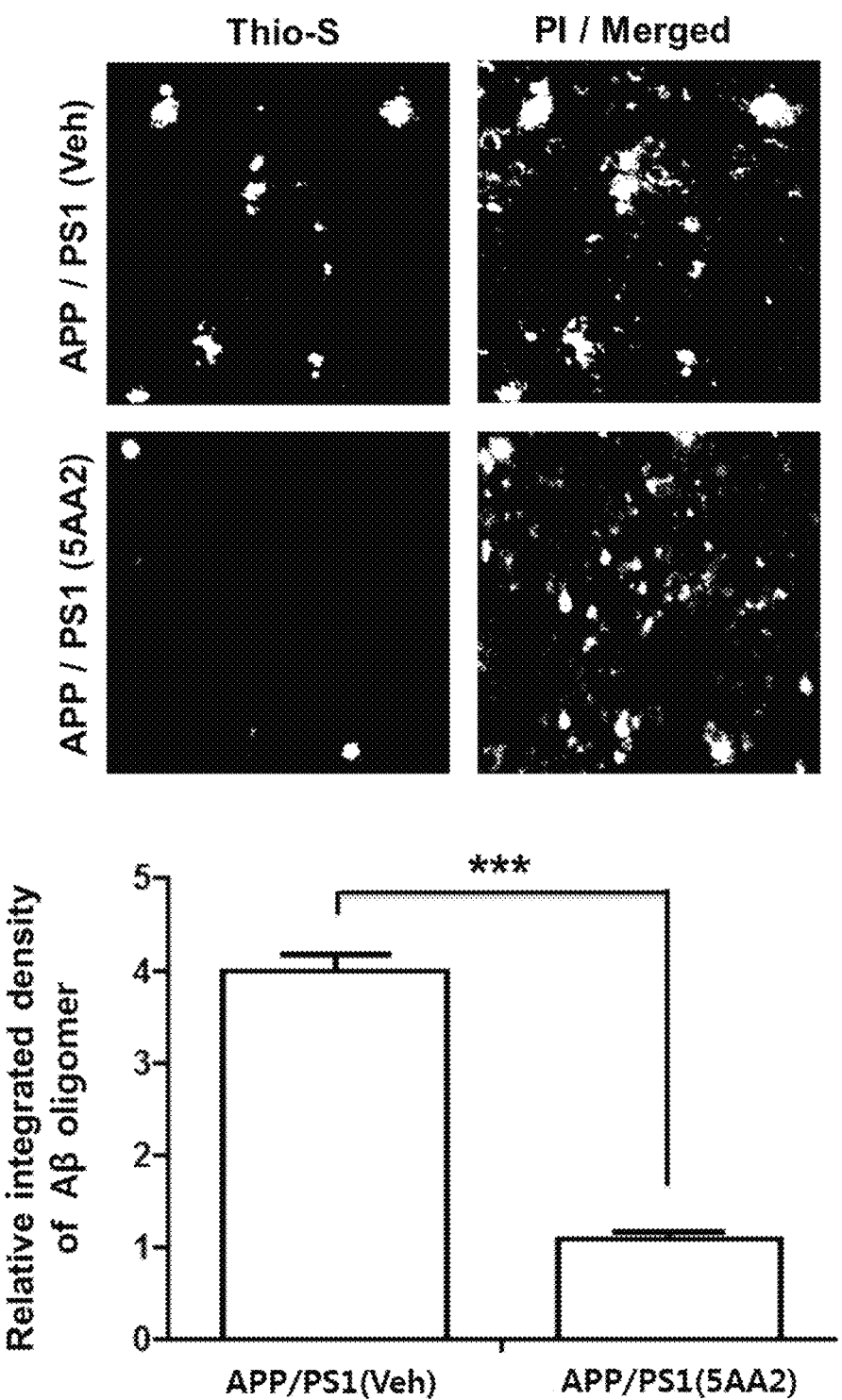
FIG. 14 shows a decrease in amyloid-β oligomer plaques increased in the cortex of APP/PS1 mice, due to the treatment with adiponectin receptor-activating novel peptide (5AA2) according to the present disclosure. Thioflavin S staining images show that the 5AA2 treatment to APP/PS1 mice significantly reduced the integrated density of the Aβ plaques as compared to the Veh-injected APP/PS1 mice. Magnification 40×. Graphs show the means±SEM for the mice (n=5/group). *** indicates that amyloid-β oligomer (Aβ oligomer) plaques expressed in the cortex of APP/PS1 mice were statistically significantly reduced due to the treatment with 5AA2 ($P<0.001$).
Figure 15:
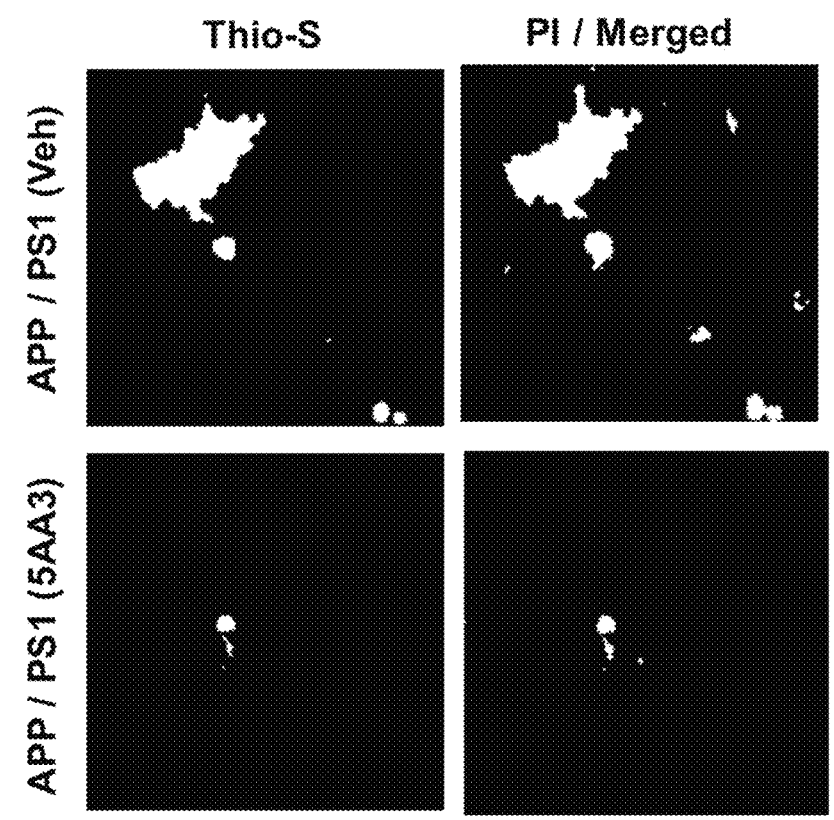
FIG. 15 shows a decrease in amyloid-β oligomer plaques increased in the cortex of APP/PS1 mice, due to the treatment with adiponectin receptor-activating novel peptide (5AA3) according to the present disclosure. Thioflavin S staining images show that 5AA3 treatment to APP/PS1 mice significantly reduced the integrated density of the Aβ plaques as compared to the Veh-injected APP/PS1 mice. Magnification 40×. Graphs show the means±SEM for the mice (n=5/group). *** indicates that amyloid-β oligomer (Aβ oligomer) plaques expressed in the cortex of APP/PS1 mice were statistically significantly reduced due to the treatment with 5AA3 ($P<0.001$).
Figure 15:
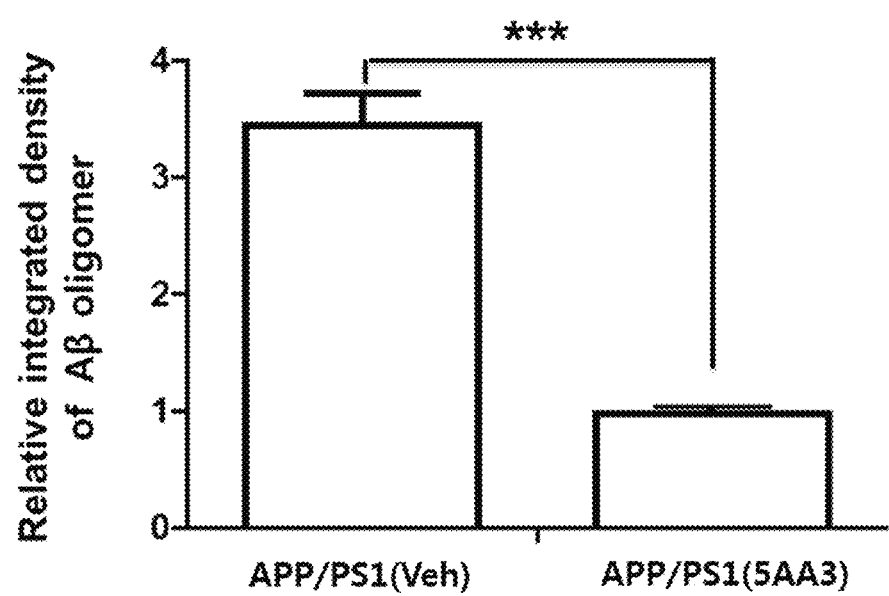
Figure 16:
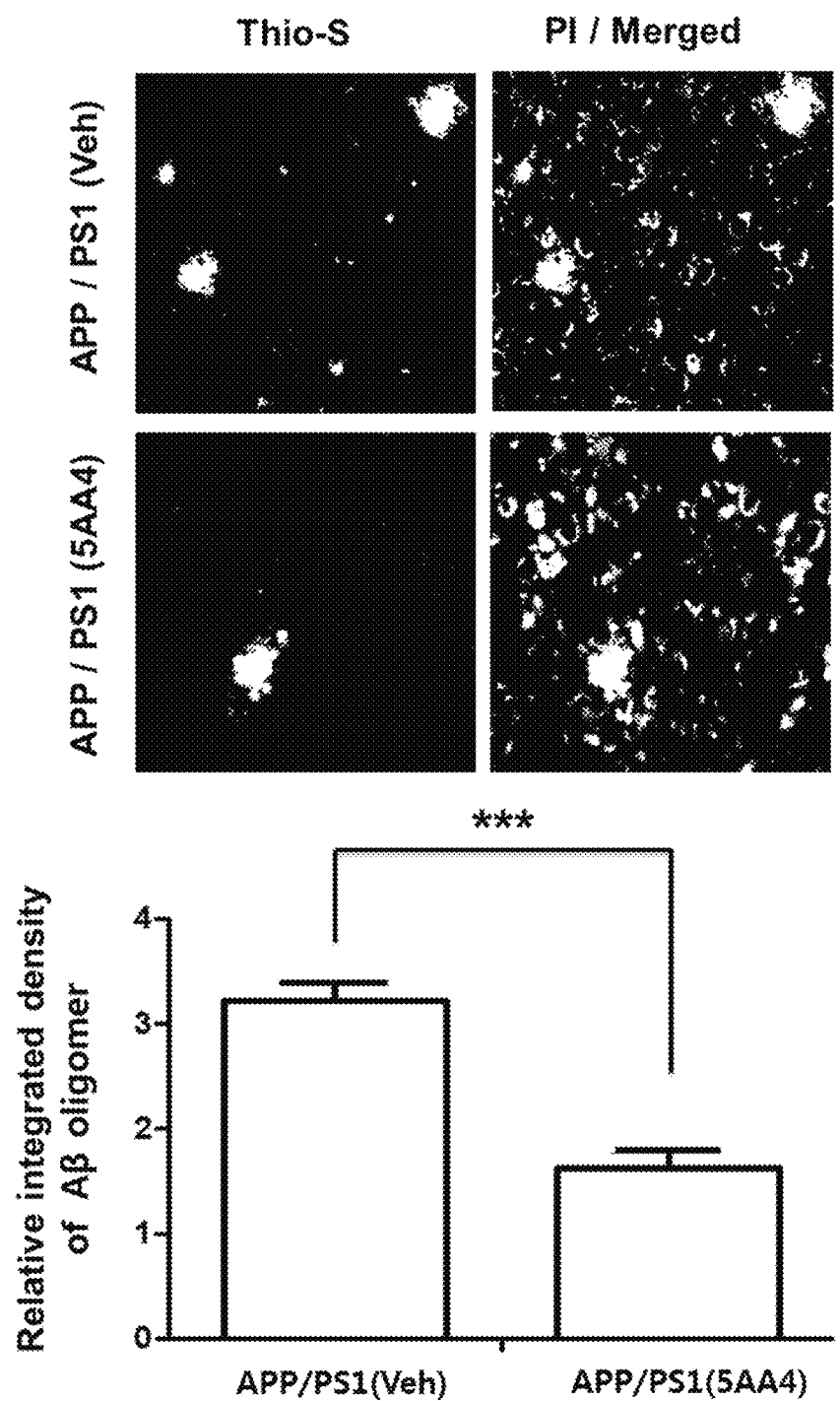
FIG. 16 shows a decrease in amyloid-β oligomer plaques increased in the cortex of APP/PS1 mice, due to the treatment with adiponectin receptor-activating novel peptide (5AA4) according to the present disclosure. Thioflavin S staining images show that 5AA4 treatment to APP/PS1 mice significantly reduced the integrated density of the Aβ plaques as compared to the Veh-injected APP/PS1 mice. Magnification 40×. Graphs show the means±SEM for the mice (n=5/group). *** indicates that amyloid-β oligomer (Aβ oligomer) plaques expressed in the cortex of APP/PS1 mice were statistically significantly reduced due to the treatment with 5AA4 ($P<0.001$).

In addition, when the cortex of the APP/PS1 model mice was treated with the adiponectin receptor-activating novel peptides (5AA2 to 5AA4) according to the present disclosure in the same manner as described above, as in the case of 5AA1, the Aβ plaque was statistically significantly decreased (FIGS. 14 to 16).

Example 5. In Vitro Electrophysiological Analysis (Long Term Potentiation: LTP)

Primary hippocampus neurons isolated from E19 Sprague-Dawley rats were cultured to a density of 150 cells/mm$^2$. AMPA receptor (AMPAR)-mediated miniature excitatory postsynaptic currents (mEPSCs) were recorded by using conventional whole-cell techniques. When primary hippocampus neurons were filled with an internal solution, the electrode resistance was varied from 3 MΩ to 5 MΩ.

The inventors of the present specification performed current measurements by using an Axopatch 200A patch-clamp amplifier (Molecular Devices, Sunnyvale, Calif.).

The voltage of the membrane and the voltage of current, commands, and digitization were adjusted by using Digidata 1322A connected to Clampex 9.2 (Molecular Devices, Sunnyvale, Calif.) of the pClamp software package on an IBM-compatible computer. The inventors of the present specification analyzed data by using Clampfit (Molecular Devices, Sunnyvale, Calif.) and Prism 4.0 (GraphPad, San Diego, Calif.). The current was low-pass filtered at 2 kHz by using an amplifiers four-pole Bessel filter.

Figure 17:
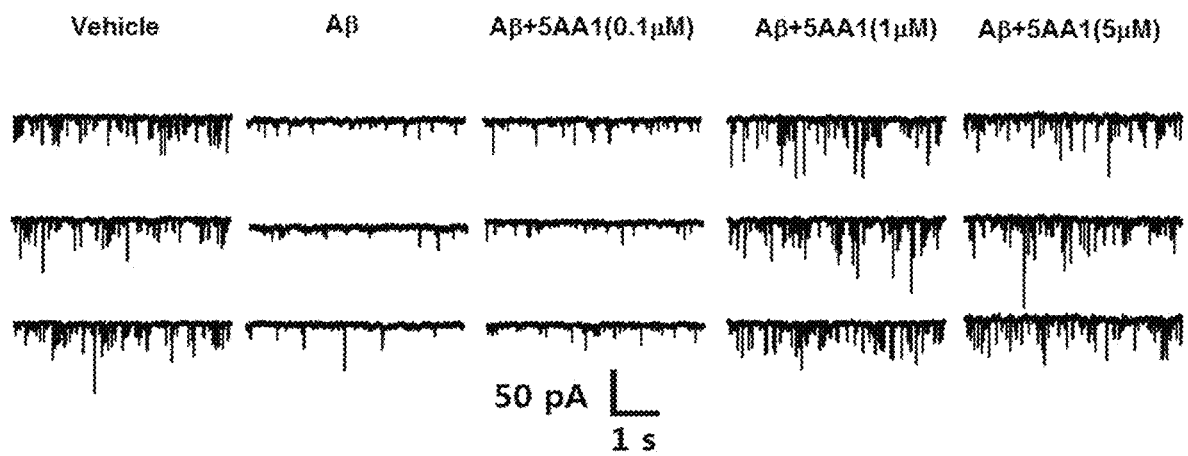
FIG. 17 shows electrophysiological measurements of LTP of cultured mouse hippocampus neurons, and identifies that mEPSC frequency (Hz) is increased in groups treated with adiponectin receptor-activating novel peptide (5AA1) according to the present disclosure at various concentrations.
Figure 17:
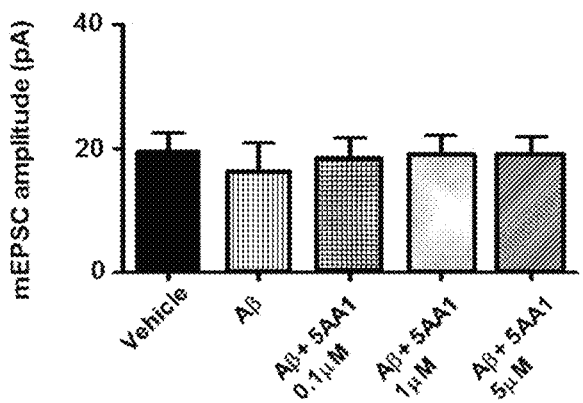
Figure 17:
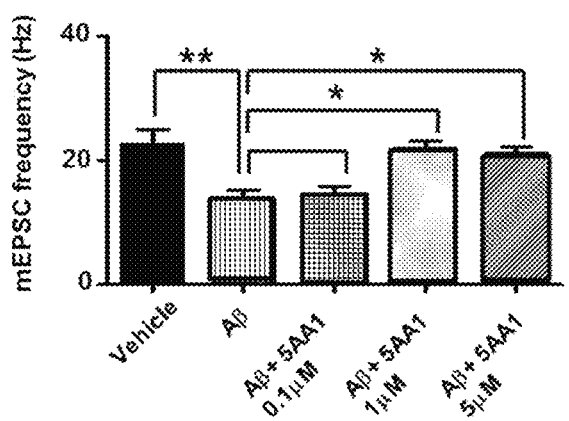

For AMPAR-mEPSCs, 1 mM tetrodotoxin was added, and the membrane potential of −70 mV, Cl$^-$ equilibrium potential in the internal and external solution configurations according to the present disclosure, was maintained to perform electrophysiological assay An intracellular recording solution (patch electrode) included 125 mM Cs methanesulfonate, 8 mM NaCl, 10 mM HEPES, 0.5 mM EGTA, 4 mM Mg-ATP, 0.3 mM Na-GTP, and 5 mM QX-315Cl (pH 7.25, titrated with CsOH, 285 mosmol$^{-1}$). An extracellular recording solution included 134 mM NaCl, 5.4 mM KCl, 2.5 mM CaCl$_2$, 1.2 mM MgCl$_2$, 10 mM D-glucose, and 10 mM HEPES (pH 7.4, titrated with NaOH). For each cell, data was filtered at 2 kHz and analyzed by using template-based miniature synaptic current detection algorithms implemented in Clampfit 9.0 software (Molecular Devices, Union City, Calif.). Each estimated mEPSC detected by software was accepted or rejected based on whether its general form was visually the same as expected for synapse phenomena. 300 consecutive mEPSCs, which conform to rise time criteria, were analyzed in each cell. The AMPAR-mediated EPSC amplitude was measured at the peak of the current at −70 mV (FIG. 17).

The cumulative probability curve of mEPSCs was calculated by using Clampfit 9.0 software and Prism 4.0 (GraphPad, San Diego, Calif.). As shown in FIG. 17, the frequency (Hz) of the Aβ group in this Example 5 was remarkably reduced compared to that of the vehicle, and the reduced frequency (Hz) was statistically significantly increased due to the treatment with 5AA1. The inventors of the present specification used Student's t-test for comparison of the two groups. Differences were considered statistically significant at $p<0.05$.

Example 6. In Vivo Electrophysiology and LTP Analysis

A hippocampus slice was prepared from adult mice to examine the CA1 circuit from the cross-sectional schaffer collateral (SC) input in the hippocampus slice (400 µM thickness). Briefly, after anesthetizing the mice with isoflurane, the brains were quickly cooled by transcardiac perfusion with ice-cold cross-cerebrospinal fluid (CSF). After the brain was removed, the brains were stored in ice-cold sucrose-artificial CSF. A coronal section was cultured in artificial CSF at a temperature of 35° C. for 30 minutes, and cultured in artificial CSF at room temperature (23° C. to 25° C.) for 1 to 4 hours before being transferred to the recording chamber. The standard artificial CSF includes 95% $O_2$ and 5% $CO_2$-saturated 119 mM NaCl, 2.5 mM KCl, 2.5 mM $CaCl_2$, 1.3 mM $MgSO_4$, 1.0 mM $NaH_2PO_4$, 26.2 mM $NaH_2CO_3$, 11 mM glucose, 1 mM Na pyruvic acid, 0.4 mM Na ascorbic acid, and the sucrose-artificial CSF includes 95% $O_2$ and 5% $CO_2$-saturated 198 mM sucrose, 2.5 mM KCl, 1 mM $NaH_2PO_4$, 26.2 mM $NaHCO_3$, 11 mM glucose, 1 mM Na pyruvic acid, and 0.4 mM Na ascorbic acid.

LTP experiments were performed at 27° C. to 29° C. For electrophysiological experiments, electrodes with a pipette resistance of 3 MΩ to 6 MΩ were used, and whole-cell recordings were obtained from neurons under visualized guidance by using infrared (IR)-differential interference contrast (DIC). The CA3 and DG regions were cleaved just before the start of LTP experiments to isolate CA1 lesions. Stimulation was applied to the shaper-side branch (SC) pathway using a concentrated bipolar electrode located at 100 to 200 mM from the soma of the recorded cells. The whole cell recording solution is as follows: 135 mM Cs methanesulfonate, 8 mM NaCl, 10 mM HEPES, 0.5 mM EGTA, 4 mM Mg-ATP, 0.3 mM Na-GTP and 5 mM QX-315 Cl (pH 7.25, titrated with CsOH, 285 mOsm) Cells were maintained at −70 mV during recording, unless otherwise indicated. The recordings were made using a multiclamp 700B (molecular devices, Sunnyvale, Calif.) which is digitized at 10 kHz and filtered at 2 kHz. Input resistance and series resistance were continuously observed during recording. The test stimulus for all EPSC experiments was set at 0.1 Hz and the duration of 0.2 ms and its intensity (100 μA to 900 μA) were adjusted to induce excitatory postsynaptic current (EPSC) amplitudes from 50 to 100 pA with a maintenance potential of −70 mV. In the LTP experiment, baseline EPSCs were measured for 3 min before applying the pairing stimuli (2 Hz, 2-minute stimulation, and post-synaptic depolarization to 0 mV). After pairing stimuli (2 Hz, 2-minute stimulation, and post-synaptic depolarization at 0 mV), EPSCs were collected every 10 minutes for 30 minutes.

Figure 18:
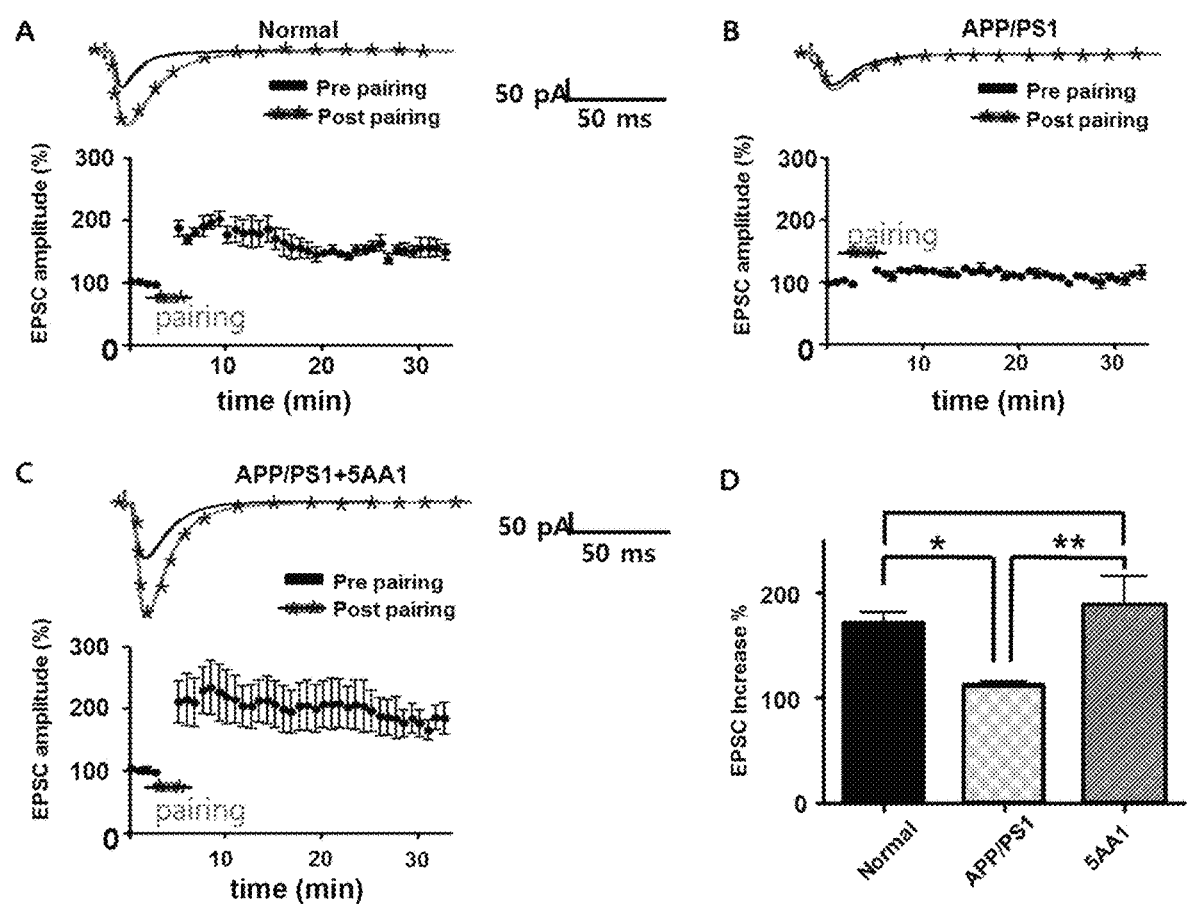
FIG. 18 shows measurements of In vivo LTP, and identifies an EPSC enhancement level of a normal group, an APP/PS1 mice model group, and an APP/PS1 mice model group, each of which was treated with adiponectin receptor-activating novel peptide (5AA1).

As a result, as shown in FIG. 18, in the normal group, synaptic transmission was enhanced in the long term by the input of pairing stimuli, and in the APP/PS1 model group, EPSC enhancement was statistically significantly decreased. When the APP/PS1 model group was treated with adiponectin receptor-activating novel peptide (5AA1), the level of EPSC enhancement was almost the same as that of the normal group.

What is claimed is:

1. A method of treating an Alzheimer's disease, the method comprising administering, to a subject in need thereof, a composition comprising at least one peptide selected from the group consisting of peptides consisting of the amino acid sequences of SEQ ID NOS: 1 to 4 as an active ingredient.

2. The method of claim 1, wherein the composition is a health functional food composition.

3. The method of claim 1, wherein an amount of the at least one peptide is in the range of 0.1% by weight to 100% by weight based on the total weight of the composition.

4. The method of claim 1, wherein the composition is prepared in any one formulation selected from a beverage, a pill, a tablet, a capsule, and a powder.

5. The method of claim 1, wherein the composition is a pharmaceutical composition.

6. The method of claim 5, wherein the pharmaceutical composition further comprises at least one carrier selected from the group consisting of pharmaceutically acceptable saline, sterilized water, a Ringer's solution, buffered saline, a dextrose solution, a maltodextrin solution, glycerol, ethanol, lactose, dextrose, sucrose, sorbitol, mannitol, starch, acacia rubber, calcium phosphate, alginate, gelatin, calcium silicate, microcrystalline cellulose, polyvinylpyrrolidone, cellulose, syrup, methyl cellulose, methylhydroxybenzoate, propylhydroxybenzoate, talc, magnesium stearate, and mineral oil.

7. The method of claim 5, wherein the pharmaceutical composition further comprises at least one adjuvant selected from the group consisting of pharmaceutically acceptable antioxidants, buffers, bacteriostats, diluents, surfactants, binders, lubricants, wetting agents, sweetening agents, flavoring agents, emulsifiers, suspending agents, and preservatives.

* * * * *